(12) United States Patent
Meisal

(10) Patent No.: US 12,059,232 B2
(45) Date of Patent: *Aug. 13, 2024

(54) SENSOR SYSTEM AND METHOD FOR CONTINUOUS AND WIRELESS MONITORING AND ANALYSIS OF HEART SOUNDS, CIRCULATORY EFFECTS AND CORE TEMPERATURE IN ORGANISMS

(71) Applicant: ONIO AS, Oslo (NO)

(72) Inventor: Kjetil Meisal, Oslo (NO)

(73) Assignee: ONiO AS, Oslo (NO)

( * ) Notice: Subject to any disclaimer, the term of this patent is extended or adjusted under 35 U.S.C. 154(b) by 545 days.

This patent is subject to a terminal disclaimer.

(21) Appl. No.: 17/282,754

(22) PCT Filed: Oct. 4, 2019

(86) PCT No.: PCT/NO2019/050210
§ 371 (c)(1),
(2) Date: Apr. 3, 2021

(87) PCT Pub. No.: WO2020/071926
PCT Pub. Date: Apr. 9, 2020

(65) Prior Publication Data
US 2022/0000376 A1    Jan. 6, 2022

(30) Foreign Application Priority Data

Oct. 4, 2018  (GB) ...................................... 1816203
Oct. 4, 2018  (NO) .................................. 20181283

(51) Int. Cl.
*A61B 5/0205*    (2006.01)
*A61B 5/00*     (2006.01)
(Continued)

(52) U.S. Cl.
CPC .......... *A61B 5/02055* (2013.01); *A61B 5/746* (2013.01); *G01K 13/20* (2021.01);
(Continued)

(58) Field of Classification Search
CPC .................. A61B 5/02055; A61B 5/28; A61B 2562/0204; A61B 2562/0271; A61B 2562/06

See application file for complete search history.

(56) References Cited

U.S. PATENT DOCUMENTS

2004/0133081 A1*  7/2004  Teller .................. A61B 5/4884
                                                              600/595
2006/0129067 A1   6/2006  Grajales et al.
(Continued)

FOREIGN PATENT DOCUMENTS

CN    105286909 A    2/2016
EP    3296708 A1     3/2018
(Continued)

OTHER PUBLICATIONS

Abiola Ayodele, PCB Layers: Everything You Need to Know, Aug. 31, 2022, https://www.wevolver.com/article/pcb-layers-everything-you-need-to-know, viewed on Oct. 20, 2023.*
(Continued)

*Primary Examiner* — James M Kish
*Assistant Examiner* — James Moss
(74) *Attorney, Agent, or Firm* — Hershkovitz & Associates, PLLC; Abe Hershkovitz

(57) ABSTRACT

A system and method for continuous readout is provided. The object of the invention is achieved by a contact surface for attaching to a surface of an organism, a sensor system in thermal, mechanical and electrical contact with the contact surface, a radio chip operatively connected to the sensor, wherein the radio chip will respond to an induced signal
(Continued)

from a reader by reading data from the sensor and transmit said data, and method for operating the sensor wherein the data from the sensor system is compensated for environmental effects using comprising a second sensor for detecting at least one property from the group comprising ambient temperature, pressure, flow, level, proximity, displacement, bio, image, gas, chemical, acceleration, orientation, humidity, moisture, impedance, capacitance, force, electric, magnetic and mass, thus forming compensated data.

31 Claims, 11 Drawing Sheets

(51) Int. Cl.
*G01K 13/20* (2021.01)
*A61B 5/282* (2021.01)
*A61B 7/04* (2006.01)

(52) U.S. Cl.
CPC .............. *A61B 5/0059* (2013.01); *A61B 5/282* (2021.01); *A61B 7/04* (2013.01); *A61B 2560/0214* (2013.01); *A61B 2562/0204* (2013.01); *A61B 2562/0219* (2013.01); *A61B 2562/0271* (2013.01); *A61B 2562/06* (2013.01); *A61B 2562/18* (2013.01)

(56) References Cited

U.S. PATENT DOCUMENTS

| | | |
|---|---|---|
| 2007/0100666 A1 | 5/2007 | Stivoric et al. |
| 2011/0137209 A1 | 6/2011 | Lahiji et al. |
| 2017/0180870 A1 | 6/2017 | Hung et al. |
| 2018/0064348 A1* | 3/2018 | Tsuchimoto ............. G01K 1/16 |
| 2018/0085062 A1 | 3/2018 | Lee |
| 2018/0146272 A1 | 5/2018 | Hung et al. |
| 2019/0000357 A1* | 1/2019 | Ross .................... A61B 5/0531 |
| 2019/0090814 A1 | 3/2019 | Lee |
| 2021/0251520 A1* | 8/2021 | Joseph .................. A61B 5/1118 |

FOREIGN PATENT DOCUMENTS

| | | |
|---|---|---|
| KR | 20130118149 A | 10/2013 |
| WO | WO 2006/062704 A1 | 6/2006 |
| WO | WO 2017/035502 A1 | 3/2017 |
| WO | WO 2018/186748 A1 | 10/2018 |

OTHER PUBLICATIONS

Examination Report in counterpart Indian Patent Application No. 202117019729, dated Nov. 24, 2022.
International Search Report in International Application No. PCT/NO2019/050210, mailed on Nov. 28, 2019.
Written Opinion of the International Searching Authority in International Application No. PCT/NO2019/050210, mailed on Nov. 28, 2019.
International Preliminary Report on Patentability in International Application No. PCT/NO2019/050210, mailed on Feb. 11, 2021.
Norwegian Search Report in related Norwegian Patent Application No. 20181283 dated Jun. 13, 2019.
English language Abstract of CN 105286909 A (Feb. 3, 2016).
English language Abstract of KR 20130118149 A (Oct. 29, 2013).
Combined Search and Examination Report in related UK Application No. GB 1816203.2, dated Apr. 3, 2019.

* cited by examiner

SENSOR SYSTEM AND METHOD FOR CONTINUOUS AND WIRELESS MONITORING AND ANALYSIS OF HEART SOUNDS, CIRCULATORY EFFECTS AND CORE TEMPERATURE IN ORGANISMS

BACKGROUND OF THE INVENTION

Field of the Invention

The invention relates to a measurement system in general and more specifically a system and a method for continuously measuring and analysing the heart sounds, circulatory effects and core temperature of an organism.

Background Art

State of the art is reflected in stethoscope, Electrocardiograph ECG, Ultrasonic imaging, sPO2, and electronic stethoscopes for heart sounds, and sPO2 for circulatory effects like oxygen saturation. For temperature measurements tympanic (in ear), oral or rectal measurements, using a manual thermometer or temporal artery infrared sensing, is considered state of the art. These methods require bulky apparatuses, handling by several professional operators, and are not suited for continuous unsupervised monitoring. In a professional care setting multi point ECG and sPO2 are used for continuous monitoring of heart rhythm and function, and respiratory function, where e.g. atrial fibrillation can develop into cardiac arrest and a potentially life threatening situation. These probes are all connected by wires, and most require that the patient is lying still while measuring, thus limiting the patient movement outside of bed, without the help of a nurse. ECG only monitors the electrical activity in the heart, limiting the use for evaluating mechanical heart function and efficacy, as e.g. cardiac Output. Since only the electrical activity is monitored alone, one can not conclude from an ECG reading that a QRS-complex actually entails a heartbeat. The inability to detect his common situation, a so called "skipped beat," with normal electrical activity but no cardiac output, is a limitation in today's ECG-evaluation.

From prior art one should refer to traditional stethoscope, traditional sPO2 and traditional thermometers and ECG.

One should also refer to WO2018/186748 regarding a system and method for continuous readout using a contact surface for a surface contact, a contact surface sensor, and a radiochip operatively connected to the sensor; and a method for measuring ambient temperature, pressure, flow, flow and flow, level, proximity, displacement, bio, image, gas, chemical, acceleration, orientation, humidity, moisture, impedance, capacitance, force, electric, magnetic and mass, thus forming compensated data.

Furthermore one should refer to EP3296708 regarding a deep body thermometer, disclosing a core body thermometer having a substrate and a heat receiving terminal with which heat flow is received and divided into two heat flows, each flow being measured by a respective heat flow measurement system that comprises an input side and an output side temperature sensor.

Finally one should refer to US2007100666 regarding a monitoring system comprises a module having at least one sensor which could be an electric-field sensor within a housing.

There is therefore a need for a method and a system to overcome the above mentioned problems.

SUMMARY OF THE INVENTION

Problems to be Solved by the Invention

Therefore, a main object of the present invention is to provide a sensor and method for continuous measuring and analysing the heart sounds, circulatory effects and core temperature of an organism.

Means for Solving the Problems

The object is achieved according to the invention by a sensor for measuring heart sounds, circulatory effects and temperature of an organism as defined in the preamble of claim 1, having the features of the characterising portion of claim 1, and a method for operating a sensor as defined in the preamble of claim 33, having the features of the characterising portion of claim 33.

In a first aspect of the invention it is provided a sensor for measuring heart sounds, circulatory effects and core temperature of an organism comprising a first layer (104) with electrodes (126) in electrical connection with the organism, a second layer (122) of an insulating material and placed on top of the first layer (104), a first temperature sensor (110) in thermal connection with the first layer (104) via the second layer (122), a second temperature sensor (120) thermally insulated from the organism is characterised by the first and second temperature sensor being located above the second layer (122), a sensor instrumental amplifier ECG device (117) connected to the electrodes (126), located on the first layer (104), where the electrodes (126) function as ECG electrodes (126), and a sound sensor (129) located on the third layer in the bottom of a cut out of the first and second layer, forming a cavity for sound to more optimally travel to the sound sensor.

Preferably the first temperature sensor (110) is in thermal connection with the first layer (104) via a thermal conductor 105 through the second layer (122). Preferably the sound sensor is a microphone. Preferably the cut out is of a conical shape.

When referring to the first, second and third layer on top of each other they are organized in a stacked fashion, where the first layer is closest to the organism. The second layer is layered on to the first layer, where the second layer is farther away from the organism than the first layer. On top of should be understood that the layers are stacked horizontally if the first layer is placed on a horizontal surface. Usually also referred to as a sandwich structure. The layers does not need to have same shape, thickness, area, orientation meaning that the layers may partially overlap while still maintaining the form of a stack of layers.

Preferably the sensor system comprises at least one additional sensor measuring additional physical property of the group comprising temperature, pressure, fluid flow, heat flow, level, proximity, displacement, bio impedance, image, light, gas, chemical, acceleration, orientation, humidity, moisture, impedance, capacitance, force, electrical, magnetic, mass and audio. Such would be advantageous of improved monitoring of the organism.

Preferably the sensor (100) is characterised by further comprising a third layer above the second layer, preferably the third and first layer comprise metallic material. One advantage is that layers can operate as capacitive storage of electrical charge.

Preferably the sensor (100) is characterised by further comprising a thin diaphragm (111) separating the organism and the cavity. Preferably this is of a thin material that resonates with body sounds, creating acoustic pressure waves to be picked up by the sound sensor (129) preferably being a microphone.

Preferably the sensor (100) is characterised by further comprising a sound sensor (129) being a accelerometer.

Preferably the sensor (100) is characterised by further comprising a sensor (111) being a piezoelectric element.

Preferably the sensor (100) is characterised by further comprising a LED (119) and a light sensor (118) on the first layer (104) pointed into the skin. Serving as a reflectance pulse oximeter.

Preferably the sensor (100) is characterised by further comprising a diaphragm (111) in connection with the surface of the organism. More preferably a sensor (128) being a accelerometer or piezoelectric component is located on the diaphragm, or built as the diaphragm. One advantage is that diaphragm movements are directly converted to an electrical signal.

Preferably the sensor (100) is characterised by further comprising a diaphragm (111) is a thin electrically conducting material, and built as a capacitive sensor in a multilayer structure. Preferably the third layer comprise a electrically conducting shape directly above the diaphragm (111) creating such capacitor. More preferably the second layer (122) between the diaphragm (111) and third layer conducting shape is removed, creating a air filled cavity for the diaphragm to move. The advantage is that a low cost structure can be implemented in standard production techniques, like PCB production. Even more preferably the first the diaphragm (111) is made of a piezoelectric element, or comprise a accelerometer mounted on it (128). The advantage is that the correlation between two sensors increase robustness and resistance to noise.

Preferably the sensor (100) is characterised by further comprising the first layer (104) to be in electrical contact with the organism, and where the sensor (128) is a Electrocardiograph ECG (instrumental amplifier with a digital converter). More preferably this ECG sensor has 2 or more electrodes separated in the first layer (104) and in contact with the organism.

Preferably the sensor (100) is characterised by further comprising a first layer (104) thermally connected with the temperature sensor (110), and electrodes (126), force sensor (115) and a light sensor (118) in contact with the surface of the organism e.g the skin of a human.

Preferably the sensor is characterised by further comprising means for harvesting electrical energy (142) and at least one energy storage unit wherein the harvested energy is stored in the energy storage unit. One advantage is that the energy can be stored for later use. The energy can be harvested from the surroundings using means for converting photovoltaic, thermoelectric, piezoelectric, electromagnetic, magnetic, electric, oxidation, electrostatic, bio-energy into electrical energy.

Preferably the sensor is characterised by further comprising means for harvesting electrical energy (142) and where the energy is harvested from the diaphragm sensor (128) being a piezoelectric element.

Preferably the sensors are characterised by further comprising processing means for sampling the ECG sensors, first and second temperature sensor, the sound sensor and the light sensor. One advantage is that the sensors data can be converted to a digital format. The processing means is programmable and alterable, where said processing means can have at least one property from the group comprising alterable mode of operation, sensor operation, store data, process data, encrypt data, decrypt data, interpret data, operate and calibrate auxiliary components and self-destruct. In addition a memory device may be provided to allow storage of sensor data for later retrieval.

Preferably the sensor is characterised in that the energy storage unit is at least one capacitive storage, preferably formed of at least two metallic layers (104, 106) and at least one insulating layer (122) of the sensor (100). The energy storage unit can also be a battery, fuel cell or similar.

Preferably the sensor is characterised in that the sensor further comprises a radiating element wherein the first layer is a reflector for the radiating element, wherein an insulating material is creates a distance between the antenna radiating element and the reflector. One advantage is a compact design.

Preferably the sensor is characterised in that the radiating element, the insulating material, and the reflector forms an energy storage unit for storing harvested energy. One advantage is improved size.

Preferably the sensor is characterised in that the reflector comprises a capacitive storage device for storing harvested energy from the energy harvesting means. One advantage would be reduced size of unit and ease of manufacturing of the device.

Preferably the sensor is characterised in that the radiating element functions as receiving element for energy harvesting. One advantage is that energy from radio waves can be harvested.

Preferably the sensor is characterised in that the processing means is coupled to at least one selected from at group comprising the energy harvesting means, energy storage unit, and capacitive storage device for powering the processing means to sample data from at least one sensor (110, 120, 115, 118, 128, 129) and the processing means is coupled to the radiating element for transmission of the at least one sampled sensor data. One advantage is that the unit can be powered from its surroundings, operate for periods without access to harvesting energy as previous energy is stored in the device.

Preferably the sensor is characterised in that the sensor further comprises an indicator coupled to the processing means, preferably a coloured light. The indicator could be a LCD screen, e-ink screen, white light or other device that can provide visual indication to a user of an alarm situation.

Preferably the sensor is characterised in that the sensor further comprises a button to be used for notifications and alarms. The notifications and alarms can be a time coded tapping sequence. The notification and alarm can be used to timestamp data of an event or call for assistance. Preferably this sensor is the same as the sound sensor (129).

In second aspect of the invention it is provided a method for measuring heart sounds, circulatory effects and core temperature of an organism using a sensor, according to claim 1, placed on the surface of the organism, wherein the method comprises the steps:

Measuring the ECG from the first sensor,
measuring the heart sound from the sound sensor,
measuring the oxygen saturation from the light sensor,
measuring the temperature from the first temperature sensor,
measuring the temperature from the second temperature sensor,
calculating the core temperature according to heat flux calculations using the measurement from the first and the second temperature sensor.
processing the sound from the microphone with respect to frequency, amplitude and phase shifts to determine heart sound classifications and heart movement.

Preferably the method comprises calculating the oxygen saturation from the delta between emitted and received light spectrum. Calculate the ECG signal and complexes from the ECG recorded data.

Preferably the method further comprises calculating the pulse and heart movement from the accelerometer data.

In a third aspect of the present invention it is provided for use of a sensor for measuring the surface temperature of an organism.

In a fourth aspect of the invention it is provided for use of a sensor measuring mechanical pressure, such as from user input, where the user pushes, taps or hits the sensor to alert a e.g. caretaker. Such taps can also be a time coded sequence to avoid false alarms.

A number of non-exhaustive embodiments, variants or alternatives of the invention are defined by the dependent claims.

The term "continuous" is in this context understood to mean a measurement system that repeatedly performs measurements, regardless of user intervention, given that the system is enabled. For monitoring ECG in humans this may mean measurements from 250 Hz to 1 kHz, to accommodate the required sampling rate relative to detect Heart Rate Variability HRV. For monitoring heart sounds in humans this may mean measurements at 4 kHz to accommodate the required sampling rate relative to detecting and separating the first, second and third heart sound, the systole and diastole sounds and the characteristics of pansystolic murmur. For oxygen saturation this may mean measurements as rarely as 1 time every 10 seconds. For monitoring body temperature in humans, this may mean measurements as rarely as 2 times each minute, to accommodate the required sampling rate relative to how fast body temperature can change and the preferable resolution of ±0.1° C. Examples of rapid changes can be caused by malignant fever, remittent fever or similar. Such rapid changes may be less than 1 degree every 10 minutes, and to accommodate Shannon's sampling theorem and detection of temperature changes within ±0.1 degree Celsius, a sampling rate of 2 samples every minute is required.

The present invention attains the above-described object by ECG electrodes, light sensor, temperature sensor and sound sensor sharing a contact surface with an organism. The contact surface provides an excellent electrical, sound and thermal contact with the organism where the ECG, heart sounds, oxygen saturation and temperature of the organism can be measured. A mixed signal semiconductor allows for the sensors and other physical parameters of the organism to be quantified, signal processed, stored and distributed. Preferably, the distribution is by means of a wireless communication link. The communication link is enabled by a central reader that generates a carrier wave and a modulated transmission. The carrier wave in turn modulated by the mixed signal semiconductor, typically used in backscatter wireless systems, for example RFID.

A sensor system for continuous readout is provided, comprising a contact surface for attaching to a surface of an organism, a sensor in electrical contact, a sensor in thermal contact, a sensor in optimized audio contact, and a sensor in optical contact with the contact surface, a RFID chip operatively connected to the sensors, wherein the RFID chip will respond to an induced signal from a reader by reading data from the sensor and transmit said data.

Preferably the system is encapsulated in a resilient material while the contact surface is exposed.

Preferably the contact surface is coated with an adhesive layer.

Preferably, the system harvests energy from it surrounding and stores it in a designated storage unit. This is advantageous in batteryless applications.

Preferably, the system is programmed and can be programmed to perform tasks as such as operate sensors, signal processing, algorithm work, data processing, store data and operate the backscatter radio based on a defined program. An example of such program could be to power up its sensor engine, record sensor data, power down sensor engine, and store the sensor data with timestamps 1 time every programmed time unit, regardless of reader contact, as long as the power is sufficient.

Preferably, the system can operate independently based on a program and operate sensors and store data such as sensor data for later readout or transmission. This is advantageous in that the system can operate autonomously.

Preferably, the system harvest energy from its surroundings and stores it in a designated energy storage unit.

Preferably, the system is programmable and can be programmed to perform tasks such as operate sensors, compute data, store data and operate the radio based on the defined program.

Preferably, the system can operate independently based on a program and operate sensors and store data for later readouts. Preferably, the system further comprises an antenna located on any side relative to the contact surface using a resilient material, wherein the distance between the antenna and the contact surface provides an antenna gain.

Preferably the system further comprises an antenna, comprising a radiating element located on a side separated from and substantially opposite to a metallic reflector. The radiating element and the metallic reflector is spaced apart by a material, where the dimension of the material defines the space between the radiating element and the reflector and the antenna gain by the electromagnetic properties of such spacing material and the radiating efficiency of the radiating element. This to reduce the absorption effects from the organism e.g. human body, mammal, animal etc. Such reflector can be implemented in such a way that it can double up as energy storage for a system, and as heat transfer element for heat flux to allow lower cost and less complex manufacturing.

Preferably, the metallic layer for the antenna is designed as a multilayer structure, where the layers are separated by an insulator and where the layers are practically implementing a single or multidimensional capacitor, to serve as an energy storage unit.

Preferably, the metallic layer serving as a metallic reflector for the antenna are designed as a multilayer structure, where the layers are separated by an insulator, to serve as a energy storage unit.

Preferably the insulator separating the metallic layers have known and constant thermal conductivity, transferring heat to the upper-most layer of the multilayer reflector structure.

Preferably, the upper layer of said structure is connected by a heat and electrically conducting material to a layer where the sensors are located. Said connection can be a thin pin or VIA connecting one temperature sensor thermally.

Preferably, an insulating material is placed between the multilayer reflector upper layer and the layer where the temperature sensors are connected.

Preferably, an additional temperature sensor is located on the upper layer of this insulator, separating the heat from the contact surface by a known and good insulator.

Preferably, the two temperature sensors are located on the same structural level to be used for performing heat flux measurements, e.g. for estimating core temperature.

Preferably the sound sensor is located on the same structural level as the temperature sensors, only located in the bottom of a cavity shaped in the other layers to optimize sound to the microphone.

Preferably the instrumental amplifier connected to the electrodes, are located on the same structural level as the temperature and sound sensor.

Preferably the light sensor is located on the structural level in contact with the skin.

Preferably the system further comprises a second sensor for detecting at least one property from a group comprising temperature, pressure, heat flow, fluid flow, level, proximity, displacement, bio, image, impedance, illumination, gas, chemical, acceleration, orientation, humidity, moisture, impedance, capacitance, resistance, force, electrical, magnetic, sound, noise, audio and mass.

Preferably the system further comprises 2 or more of the same sensor, forming a cluster of sensors.

The cluster of sensors can be used together to measure complex value such as flow or combined to compensate for environmental impact such as drift and noise.

Preferably, a combination of sensors for temperature, moisture and bio impedance can be of great value for detecting sweat, dehydration, and fever in one. Enabling care for fever and preventing patients from laying soaking in sweat, and providing advice to levels of hydration necessary for ill patients which can be critical with e.g. elderly patients.

Preferably a combination of one or more temperature sensors and an acceleration sensor is used to detect fever cramps and spasms of the organism.

Preferably a combination with a capacitance sensor can e.g. detect that the sensor has been placed on skin, and e.g. enable touch capability for e.g. on/off functionality.

Preferably the system further comprises a positional detector.

In some embodiments a method for operating a sensor is provided, wherein the data from the sensor is compensated for environmental effects using a second sensor for detecting at least one property from a group comprising temperature, pressure, flow, level, proximity, displacement, bio, image, gas, chemical, acceleration, orientation, humidity, moisture, impedance, capacitance, force, electric, magnetic, and mass, thus forming compensated data. Preferably from the group further comprising a combination of e.g. carolis flow sensor, and two accelerometers a low cost blood flow and pressure sensor can be implemented providing low cost, comfortable, non invasive mean for continuous monitoring for home use for e.g. patients being subscribed with beta blockers.

Preferably, an alarm is raised when the recorded sound from the sound sensor is outside a predefined range, e.g. when the hear sound frequency content shows a highly elevated component above 150 Hz, indicating a pansystolic murmur.

Preferably, and alarm is raised when the data from the sensor is outside a predefined range, e.g. when the fever rise above 39° C., or when the heart rate is highly increased, or combinations of the two.

Preferably, and alarm is raised when the data from the sensor is outside a predefined range, e.g. when the temperature rises from a stable temperature between 36 and 37.9 degrees, to above 38° C., indication a sub febrile state or possible febrile state.

Preferably, and alarm is raised when the data from the sensor is outside a predefined range, e.g. when the fever rise from a temperature under 38.5° C. to above 38.5° C., indication a definite fever.

Preferably an alarm is raised when the compensated data from the sensor is outside a predefined range, e.g. when ambient temperature is above 35° C.

Preferably, an alarm is raised when the data from the second sensor is outside a predefined range, e.g. when temperature is above 45° C.

Preferably, an alarm is raised when the combined data from two or more sensors are outside a predefined range, e.g. when fever is high in combination with high ambient temperature and high heart rate. E.g. fever of 40° C. in combination with heart rate of 100 and ambient temperature above 35° C.

A sensor system and method for continuous and wireless measuring heart sounds, circulatory effects, oxygen saturation and core temperature in organisms, such system comprises of a wireless sensor system integrated preferably as a flexible adhesive bandage, which is placed on the surface or skin of an organism. Preferably, the system is provided with means for energy harvesting from its surroundings and means for storing the harvested energy in a energy storage unit. Such energy harvesting can be implemented as rectification a carrier wave used in wireless communication or rectification of terrestrial broadcast signals such as radio or TV bands. The harvested energy is stored in the energy storage unit such as capacitor, rechargeable battery or similar storage unit for storing electrical energy for later use. An alternative system is capable of boosting the small electrical potential from a photovoltaic cell or a more traditional fuel cell. The capacitor can be as previously mentioned be realized by means of the two metal bodies (layers) already used for temperature flux measurements A wireless reader capable of reading sensor data using a defined radio protocol, or several protocols in combination, in addition to e.g. sensing ambient conditions, and transmitting such data to an ecosystem which can be implemented as a e.g. network cloud solution, and said ecosystem with methods and signal processing for presenting simplified quantifiable data to an end user device and enabling individualized adjustable notifications based on such data, access to history of data as well as a big data access platform to such ecosystem, with methods for analysis which can be used for location, tracking and new insight in information on the conjunction between heart sounds, oxygen saturation and temperature in organisms and trends, one of these uses can be monitoring illness causing increased temperature usually referenced to as fever in an organism in conjunction with heart sounds, e.g. in a human having, caused by e.g. infections, as e.g. endocarditis. Combining user provided information on the organism, and its geolocation, which e.g. can be derived from the user device, for additional analyses can have one example of tracking geo located data and infection patterns through such ecosystem. One example can be tracking asthmatic outbreaks in humans, and spread in the society using geolocation and the characteristics of the heart sounds and frequency content response over time, which can map to environmental causes of heart conditions. Such use would be of great value to health care authorities and medical research and can contribute greatly to the knowledge on registered and unregistered illness in the society with respect to; infection source tracking, infection spread tracking and generally increased knowledge on registered and unregistered illness causing febrile responses, characteristic heart sounds and accompanied changes in heart rate and oxygen saturation. As an example, such device can be used in both developed and undeveloped parts of the world to improve knowledge, countermeasures and aid in both epidemic and non-epidemic outbreaks.

Effects of the Invention

The technical differences over prior art is that it is possible to wear the sensor system continuously without discomfort and the sensor has a higher degree of integration and precision of measurement. Other technical differences are the sensor is provided with means for energy harvesting and storage of energy. The reflective layer in the sensor also effectively shields the radiating element from the electrical absorption in the skin creating an improved antenna system.

These effects provide in turn several further advantageous effects:

- it makes it possible to monitor an organism continuously, such as humans and animals,
- it makes it possible to use the measurement system continuously and without supervision by a caretaker or patient,
- it allows for valid reading of sensor also in the presence of varying ambient temperature, sound, moisture and even when covered,
- it allows for continuous measurements, even if the reader or power source is out of range,
- it allows for a wireless and passive sensor integration at low cost, which enable consumable heart sound sensors limiting infection risks and faulty sensors with reuse,
- it allows for ECG and heart sounds patterns and oxygen saturation and fewer patterns to be used as an indication to identify heart and cardiac illness and failure, and infectious and non-infectious diseases in organisms,
- it allows for anomalies in ECG, heart sounds and body temperature, like increased heart frequency, strange or missing sounds or changes in amplitude of normal baseline temperature variations to be detected, as an early warning of sepsis developing in e.g. neutropenic patients,
- it allows for temperature alerts on e.g. high and low temperatures and without supervision,
- it allows for heart rate alerts on e.g. high and low heart rate and without supervision,
- it allows for changing ECG and heart sound correlation on e.g. HRV and heart failure and without supervision,
- it allows for a low cost sensor enabling widespread use in professional and domestic health care settings,
- it allows for non-invasive monitoring of organisms,
- it allows for a more comfortable monitoring of patients and organisms, e.g. critically ill patients,
- it allows for a simple visual feedback from the reader or the sensor to signal alarm/no-alarm condition,
- it allows for reduced reliance on one-time use power sources as battery,
- it allows for an easy to use monitoring system,
- it allows for a more efficient system to monitor organisms, and
- it allows for a smaller system for monitoring of organisms.
- it allows for heart sounds related to known illness to be monitored and detected without supervision,
- it allows for accompanied heart rate related to known illness to be monitored and detected without supervision,
- it allows for patient to notify or alarm caretaker through pushing or tapping the sensor implementation,
- it allows for user to timestamp events to data through pushing or tapping the sensor implementation without the need for supervision,
- it allows for heart frequency monitoring without the need for supervision,
- it allows for heart rate monitoring without the need for supervision,
- it allows for heart sound frequency monitoring without the need for supervision.

BRIEF DESCRIPTION OF THE DRAWINGS

The above and further features of the invention are set forth with particularity in the appended claims and together with advantages thereof will become clearer from consideration of the following detailed description of an embodiment of the invention given with reference to the accompanying drawings.

The invention will be further described below in connection with exemplary embodiments which are schematically shown in the drawings, wherein.

DESCRIPTION OF THE REFERENCE SIGNS

Figure 1:
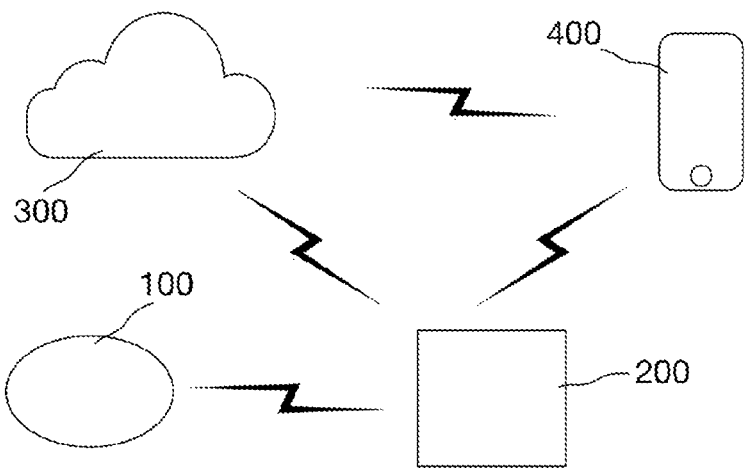
FIG. 1 shows a system comprising sensor implementation, reader, ecosystem and user device.
Figure 2:
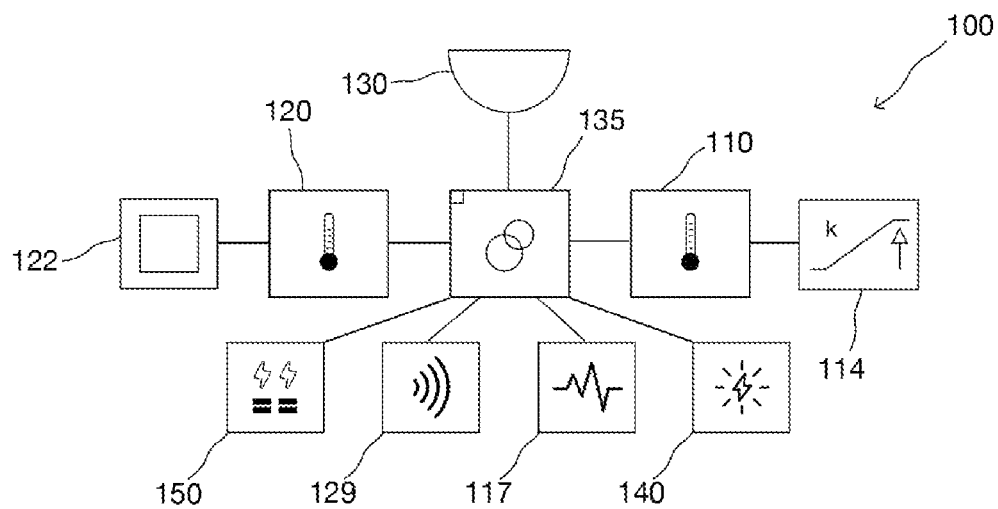
FIG. 2 shows the sensor implementation with antenna, radio chip, sensors, energy harvesting, thermal conductor, thermal insulator and energy storage.
Figure 3:
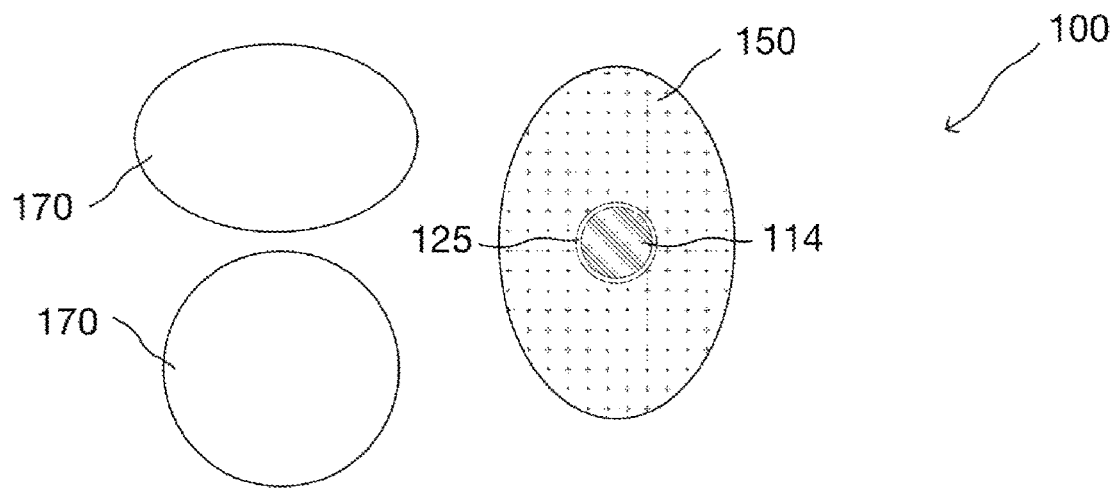
FIG. 3 shows the sensor implementation and examples of shapes and the space between thermal conductor and adhesive.

The following reference numbers and signs refer to the drawings:

| | |
|---|---|
| 100 | The sensor implementation with the antenna, radio chip, sensors and thermal conductor |
| 101 | Bonding wire |
| 102 | Bonding wire connected to RF rectifier |
| 103 | Copper (CU) top layer heat conductor to ambient |
| 104 | Exposed metal connected to contact surface |
| 105 | PCB Via operating as a heat pipe/conductor |
| 106 | Metal layer |
| 107 | PCB VIA operating as an electrical connection only, not heat pipe/conductor |
| 108 | Air Cavity |
| 109 | Cap back plate |
| 110 | Temperature sensor connected to radio chip |
| 111 | Diaphragm |
| 112 | Perforation for airflow |
| 113 | Cone shaped cavity |
| 114 | Thermal conductor |
| 115 | Force sensor |
| 117 | ECG voltage sensors |
| 118 | Light sensor |
| 119 | Light source/LED |
| 120 | Temperature sensor connected to the radio chip |
| 122 | The thermal insulator, substrate |
| 124 | Heat flux between the two thermistors |
| 125 | The space/gap between the thermal conductor and the metal backing and adhesive under the antenna part of the sensor implementation |
| 126 | Electrodes |
| 128 | Accelerometer |
| 129 | Sound sensor |
| 130 | The antenna part of the sensor implementation |
| 132 | The dedicated antenna area of top layer |
| 133 | The transition and connection to a thermistor on the bottom layer |
| 135 | The radio, protocol and controller part of the sensor implementation |
| 137 | The cut out in the antenna area in the design, where the connection to the second sensor are routed |
| 138 | The metallic reflector part of the antenna |
| 139 | The cut out in the metallic reflector to fit the connection to the thermal conductor |
| 140 | The energy harvesting part of the sensor implementation |
| 142 | The dedicated energy harvesting area of the top layer |
| 144 | The print layer of the sensor implementation |
| 150 | Energy storage part of the sensor implementation |
| 152 | The adhesive fixing the sensor implementation to the measured surface |
| 155 | The cut out in the adhesive, where the thermal conductor connection to the skin is located |
| 170 | The sensor implementation and some examples of shape variations |
| 180 | The main substrate where the sensors chips and antenna are embedded |
| 182 | The connection wiring between two sensors |
| 200 | The reader with antennas, radio reader chip, processing chip, interfaces, data storage, sensors and airflow design |
| 210 | The radio reader chip |

| | |
|---|---|
| 220 | The radio reader antenna |
| 230 | The processing and interface chip |
| 240 | The data storage in the reader |
| 250 | The readers wired interfaces |
| 260 | The antennas for the reader wireless interfaces |
| 270 | The ambient sensors in the reader |
| 280 | The airflow design for the reader ambient sensors |
| 290 | The radio for wireless interfaces |
| 300 | The ecosystem with interfaces, signal processing algorithms, processing and storage systems |
| 310 | The ecosystems user storage |
| 320 | The ecosystems sensor data storage |
| 330 | The ecosystems product database |
| 340 | The ecosystem interface for Big data access |
| 350 | The ecosystem interface for end user access |
| 360 | The ecosystem processing unit |
| 370 | The ecosystem signal processing algorithms |
| 400 | The end user device |
| 420 | The end user device with application or web browser, and its storage unit |
| 422 | The end user device with application or web browser |
| 424 | The storage unit in the end user device |
| 500 | The Temperature heat flux measurement setup |
| 510 | Tissue/skin heat transfer coefficient |
| 515 | Heat Flux between core and tissue/skin |
| 520 | Core Temperature $T_C$ |
| 530 | The human body thorax |
| 610 | Air in measurement environment |
| 615 | Heat flux between sensor 100 and environment |

DETAILED DESCRIPTION OF THE INVENTION

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The invention will be further described in connection with exemplary embodiments which are schematically shown in the drawings.

For the apparatus presented in FIG. 1 being an e.g. heart sounds, heart rate, ECG, oxygen saturation and core temperature monitoring system intended for professional and home use by patients suspecting a heart condition or when subscribed by a professional. The alternatives that exist and are mostly used today for heart monitoring and oxygen saturation are more expensive ECG apparatuses, stethoscopes and sPO2 sensors, requiring wired and/or bulky apparatuses to be worn, and in some cases for batteries to be changed or charged. for temperature, Tympanic (in ear), oral or rectal measurements, and temporal artery infrared sensing. By most these are considered uncomfortable and tedious to wear and manage e.g. extra effort when taking a shower. The most comfortable approach existing is the temporal artery infrared sensing approach, however this does not allow continuous measurements. A few Bluetooth based devices allowing continuous measurements has emerged, however these comprise batteries and some electronics, which will make the total cost of ownership for a consumer to high for widespread use. The fact that these devices are based on Bluetooth, makes them less user friendly, as it limits the user device to be within range of the sensor, which can be a challenge in environments with building materials like reinforced concrete. It also limits the number of sensors that a user can observer continuously. This results in that the user and the user device needing to stay in the same room as the sensor in order for the user device to get continuous data from the sensor and alarms. Backscatter radio technology, is best known in the form of RFID, which has existed for years and are in most approaches designed for electronic identification in large logistics operations and security applications in some form, where you have a reader infrastructure reading large volumes of tags.

Principles Forming the Basis of the Invention

The underlying principle is that a wearable sensor can be used for continuous monitoring by integrating sensors with backscatter radio and antenna into a low cost sensor system without batteries, in a packaging with an adhesive for attachment to a surface of an organism. A reader utilizing the same backscatter radio technology induces power to the sensor system and reads the available data from the sensors. In use the sensor system can be repeatable read by a reader and thus allows for practical low cost and continuous use, enabling a broad area of use and more substantial amount of sensor data from areas where continuous data on a big scale has never been available. The system comprises a heart sound sensor, a heart rate sensor and, a ECG sensor, a oxygen saturation sensor, a microphone and one or more temperature sensors that are easy to manufacture using easy accessible manufacturing processes, such as traditional printed circuit boards. The preferred hearty sound sensor comprises a sound sensitive capacitor. Preferably assembled as a conductive diaphragm on the first layer in direct contact with the skin, and a metal layer on the third layer separated by an air cavity. Preferably the metal layer on the third layer is perforated by a small hole to let air flow in and out as the diaphragm moves. The preferred heart rate sensor comprises 2 or more electrodes on the first layer in electric contact with the skin. Preferrably these electrodes are connected to an instrumental amplifier followed by an analog to digital converter, the ECG. The preferred ECG sensor comprises 4 measurement points, the preferred microphone comprises a resonant cone cavity optimized for heart sounds, the preferred temperature sensor comprises an arrangement of two thermistors. Closest to the surface of the organism is a metal layer with one ECG sensor and one thermistor thermally connected to it. Then there is a layer of a material with known and preferably constant thermal coefficient. As a third layer is a second metal layer with a second thermistor thermally connected to the third layer, and a microphone connected and located in a coned cavity shaped in the insulating material. By measuring the ECG and microphone with a suitable analogue to digital converter, the heart sounds can be derived, and by measuring the thermistor values with a suitable analogue to digital converter, the heat flux can be deduced and a suitable algorithm can be applied to calculate the core temperature and heart sounds characteristics. The metal layer in the first and third layer can have arbitrary shape, preferably the metal layer in the first and third layer have corresponding shape. Preferably, the two metal layers have as much as possible overlap. Instead of having to use cumbersome techniques where the first thermistor is buried in between the first and the third layer a novel use of PCB vias is applied. The via are used as a heat pipe so that both thermistors can be on the same PCB level. This is also valid for the ECG sensor, as the contact points or electrodes can be located on the first layer and the electronics on the third, interconnected by Vias. The microphone can also be located on the third layer, in the bottom of a cone cavity, shaped to improve heart sound detection. The sensor system is particularly compact in size, easy to manufacture, and low cost using few components.

The function of the thyroid in the human body is among other things to regulate the metabolism with hormones increasing the rate as well as effecting almost all body tissues. Thyroid hormones also effect the cardiovascular system directly, increasing the strength and rate of heartbeats HR, rate of breathing RR, intake and consumption of oxygen and the activity of mitochondria. Combined increasing blood flow and Body Temperature BT.

The thyroid function response determines your bodies response to particular diet, e.g. Low Carb, High Protein, and so forth. Hence monitoring BT (and skin temperature), HR and RR after a diet intake can be applied to detect and classify your particular diet, as well as your bodies response to it. This allows a dietary monitoring system with possibilities to give dietary advice. For countries suffering with obesity or wrong nutrition such system could both be an easy way for individuals to get an insight in own dietary challenges, as well as means for guided correcting measures. Another use can be high performance athletes needing a high performance diet and body response to increase their strength or fatigue. Another is monitoring of sufficient dietary intake of patients such as psychiatric and elderly care patients.

BEST MODES OF CARRYING OUT THE INVENTION

The embodiment of the apparatus according to the invention shown in FIG. 1 comprises a flexible sensor implementation 100, a radio reader 200 that reads sensor data and stores it in an ecosystem 300 comprising data processing and presentation formatting, and presents the data to a user through a user device 400, which can be an application on a cellular phone. Such system described can be a heart sound, heart rate and temperature sensor implementation 100, where the system is designed to record heart sounds, heart rate and measure surface temperature on the thorax of a human being, for instance a child, and detect possible heart anomalies related to illness, calculate heart sound, heart rate, and calculate the core temperature of the human using the ecosystem and present this in a continuous manner to e.g. parents or alternative caretakers, and serve as an apparatus for continuous vital sign monitoring during illness, focused on heart sounds, heart rate, ECG, oxygen saturation and fever monitoring to provide continuous information on the development, trend, and severity of such development. When a medical physician is contacted due to an illness causing a heart, heart rate or febrile response, such data can be presented and analysed to aid the medical physician in a diagnosis process. Such a system would be available to a consumer through e.g. online stores, pharmacies, or a local supermarket, where the consumer would expect to find other monitoring equipment, such as fever thermometers. Available product bundles could be a reader together with several sensors, and bundles of several sensors with e.g. different print on. Such an apparatus would not only improve monitoring during illness, and care for sick children, bringing peace of mind to both the child and parent. It could also be a new unexplored area for research on illness causing heart responses, changes in heart rate, oxygen saturation and febrile response, as such scale of data on development of illness does not exist today. Most available continuous, heart, oxygen saturation and fever monitoring data today are from monitoring on sick patients in a hospital. Monitoring spread of illness in the society could have a great socioeconomic value, through reducing or preventing large outbreaks in an early stage.

The system presented in FIG. 1 is designed for continuous, wireless monitoring and analysis of heart sounds, heart rate, oxygen saturation and temperature in organisms, e.g. humans and animals. This system comprises of a flexible sensor implementation 100 e.g. like an adhesive bandage, shaped in anyway, e.g. circular, square, rectangle or oval, that can harvest energy from its surroundings, record heart sounds, heart rate, oxygen saturation and sense the temperature and wirelessly transmit it. The harvesting of energy can be induced radio waves, received solar energy, thermal energy converted to electrical energy via peltier elements where temperature difference between skin and air is used to generate electrical energy, electrical energy converted from movement via e.g. piezoelectric devices. A reader 200 that can wirelessly transfer energy to the sensor system and receive the transmission from the sensor implementation 100, add ambient sensor information like e.g. temperature and humidity from internal sensor 270, and send this to an ecosystem 300, which can be implemented in e.g. a network cloud solution. This ecosystem implementation will have methods for storing and for quantifying data and send data to the end user, preferably in real-time. The end user will interface the system through a device 400, e.g. through an application on a device like a smartphone or a web interface through any computer. The reader 200 can also as a backup solution when there is no connection to the ecosystem, transfer the data directly to the device using a wireless technology like e.g. Bluetooth, where an example can be the application on the user's device, which also have methods for quantifying the data in real time and presenting it to the user, receives and processes the data. In the backup scenario, the data is stored in the data storage unit of the device for later syncing with the ecosystem. If the reader during shorter periods loses connection with the ecosystem or device in backup mode, it has the means through internal storage to store data until connection with the ecosystem or device in backup mode is working again.

Figure 4:
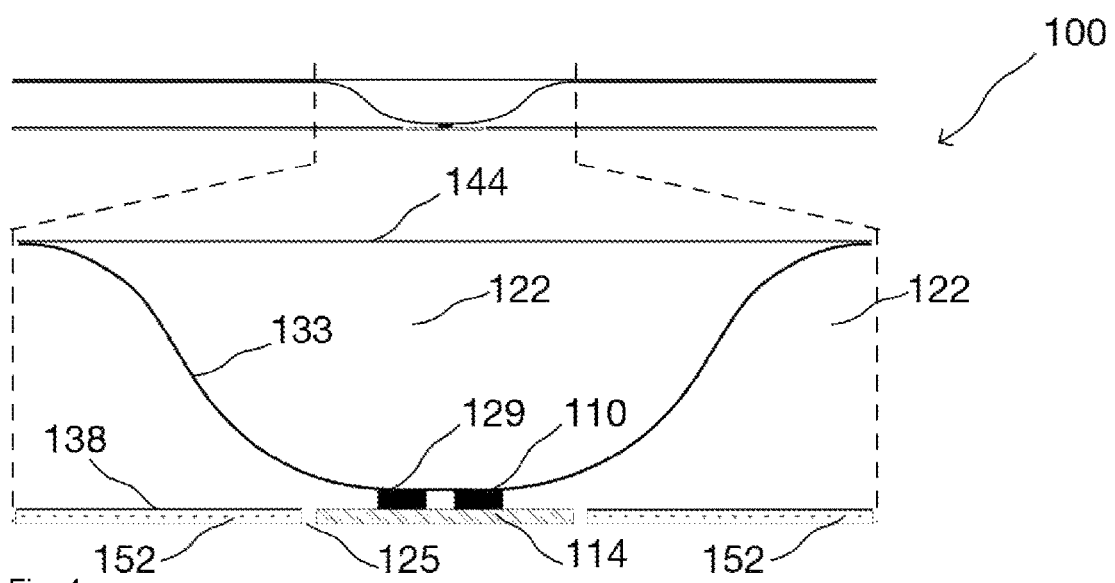
FIG. 4 shows the thermal conducting layer connected to the sensor, and the connection to the antennas and insulating layer surrounding the sensors
Figure 5:
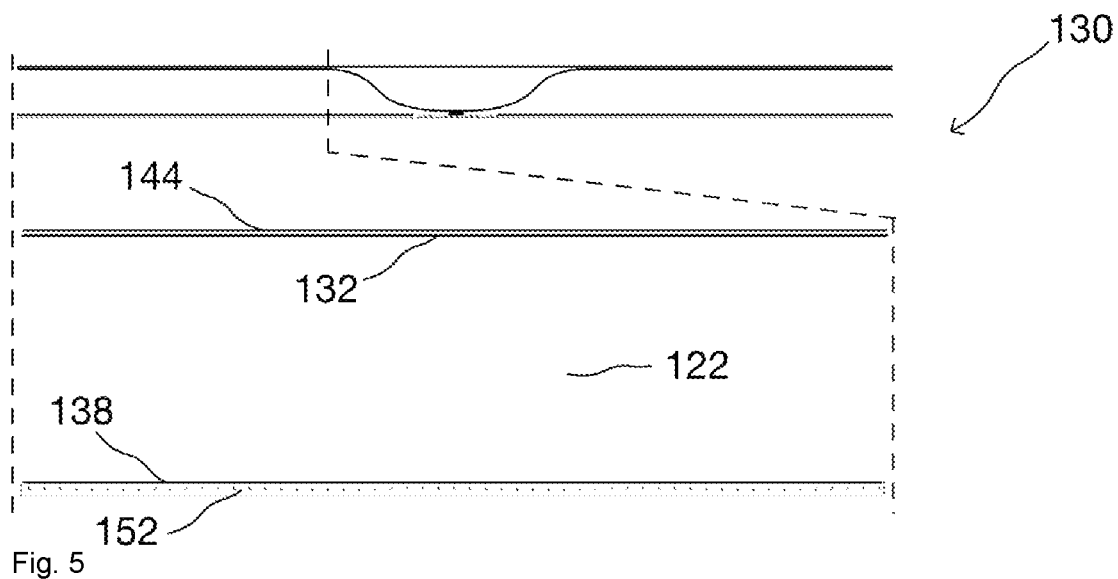
FIG. 5 shows the antenna part of the sensor implementation, with the spacing material and metal reflector.

The sensor implementation 100 is the key to the system and is built as a multi-layer structure to combine properties of long range backscatter communication and optimized sensing conditions. This can be achieved in several ways, where a first approach can be e.g. a dual sensor approach with an sound sensor in combination with a temperature sensor as illustrated in FIGS. 4 and 5, and a second approach can be a sound sensor and temperature sensing using dual sensor implementation using temperature heat flux measurement 500 as illustrated in FIGS. 2, 6, 7, 12, 13, 14, 15, 16 and 17. The sensor implementation 100 shown in FIG. 2 comprises an antenna 130, a radio chip 135 which could comprise both an integrated temperature sensing functionality, and an radio and protocol part, including a possible interface to e.g. power and communication with external sensors 110, 120, which can be a temperature sensor, 129 which can be a sound sensor, and number of ecg, which can be a voltage sensor using instrumental amplifiers, like ECG. A thermal conductive layer 114, a thermally insulating layer 122, and a print layer 144. The sensor implementation may also comprise an energy harvesting unit 140 that can harvest energy from the surroundings.

The antenna 130 is designed in such a way that it is minimally affected by the absorption of the radiated energy caused by the properties of e.g. the skin and human body. Such feature is obtained by designing the antenna 130 in a way that limits such absorption of energy. Approaches to cope with this can be one or a combination of the following; separating the antenna radiating element 132 from the skin by a given distance using spacing material 122, applying spacing material with a selected electromagnetic properties, changing the resonant frequency of the antenna, applying a metal reflector 138 between the antenna and the skin, or other approaches known by the skilled in the art. The antenna 130 will hence be designed in such a way that it is either immune to the material that it is placed onto, or that it constructively uses the features of the material that it is placed onto to improve its radiating performance.

Figure 6:
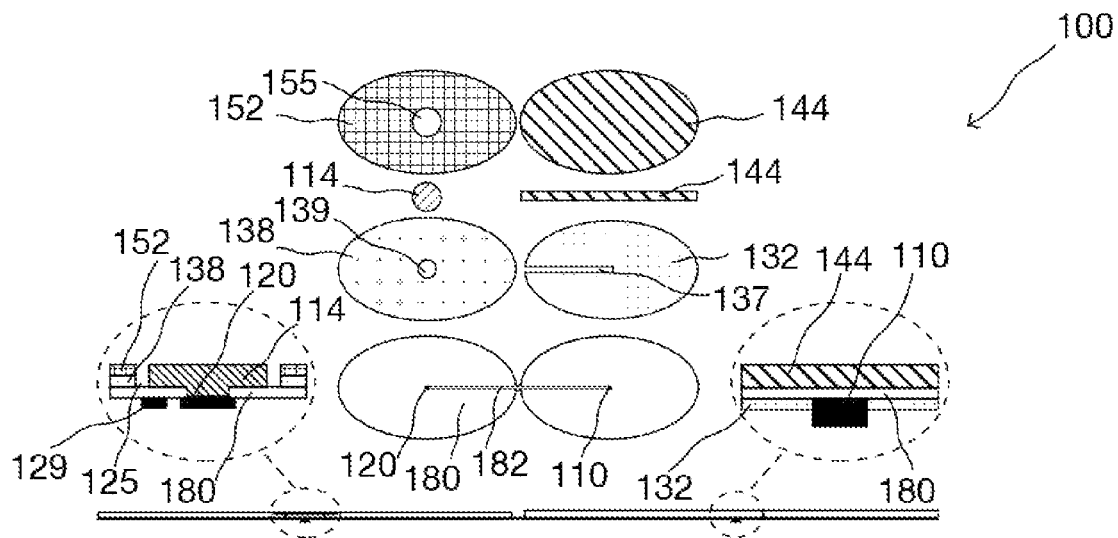
FIG. 6 shows the sensor implementation build-up and parts for heat flux mode measurement, for heart sound measurement, and heart-rate measurement.

FIG. 6 shows the thermally conductive layer 114 in the sensor implementation enables direct and good thermal contact with the surface, e.g. human skin the sensor implementation 100 is placed on. The thermal conductor 114 can be placed in a cut out area 155 of the adhesive layer 152 and cut out area 137 of the metallic reflector 138, with a space/gap 125 which can be designed in between the thermally conductive layer 114 and the lower metallic layer/metallic reflector 138 of the antenna design 130 in order to avoid a good thermal connection and electrical connection between the thermal conductor 114 and metallic reflector 138, avoiding lateral heat loss or heat transfer to 138, and reducing ESD challenges for the radio chip 135 and external sensor 110, 120, and 129. The thermally conductive layer 114 will be in direct contact with the measured medium, and the radio chip 135 with the integrated sensor and external sensor 110 in single sensor mode, and the external sensor 120 in heat flux temperature sensing mode, is thermally connected to thermally conductive layer 114 using a thermally conductive glue or similar compound both fixing the radio chip 135 and external sensor 110, and 120 and 129 as well as being a good thermal conductor. Both the radio chip 135 and sensors 110, and 120 and 129 will be in DIE form or other packaging with good thermal conductivity. The thermal connection to the sensor 120 could be made through e.g. a perforated area in e.g. a PET substrate, which could be filled with the thermally conductive glue used to fix the thermal conductor 114 to the sensor 120.

Figure 7:
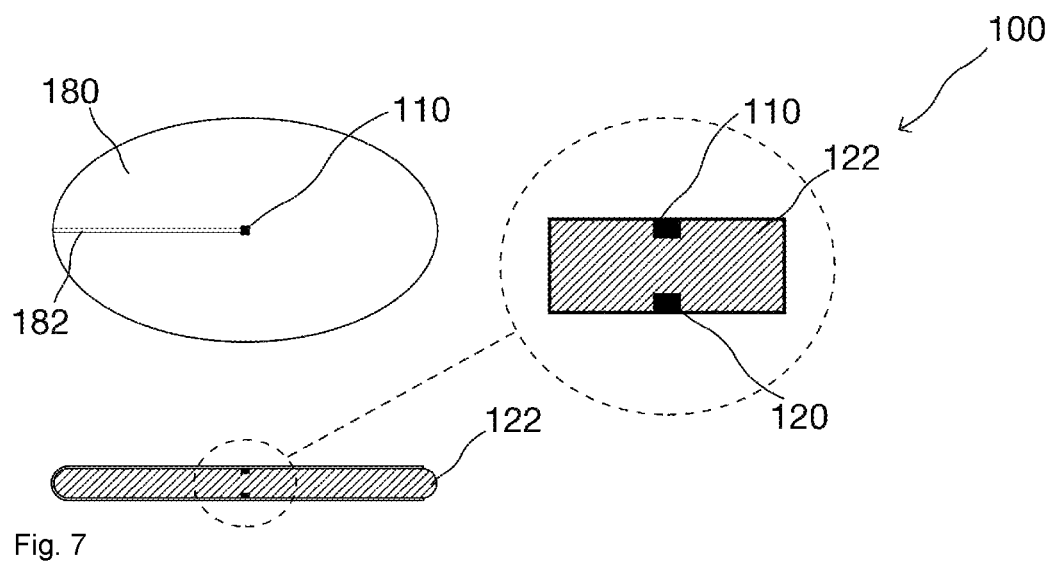
FIG. 7 shows the basic folding of substrate with radio chip and external sensor mounted around the insulator material for heat flux mode measurements.

The transition 133 from the antenna radiating element 132 on the top layer of the sensor implementation to the connection of the radio chip 135 in the single sensor approach as shown in FIG. 5, or the folding of the substrate around 122 illustrated in FIGS. 6 and 7, enables the combination of two features; good range performance in an antenna placed on conducting or absorbing surfaces, and good thermal contact between the internal sensor and the sensors 110 and 120 and the measured medium. Referring to FIGS. 4 and 5. The transition 133 from the antenna radiating element 132 to the lower layer of the sensor implementation in the single temperature sensor approach is optimally shaped as e.g. a planar cut of a sphere, as an arc where the radio chip 135 and sound sensor 129 is located at the centre bottom of this shape. The bottom centre of the shape is located at one of the lowest layer in the sensor implementation 100, while the antenna radiating element 132 connected to the outer edge of this shape is located at the second layer from the top, directly under the print layer 144. The substrate comprising the antenna radiating element 132 and the shaped transition 133 and the connected radio chip 135 is one piece, assembled on e.g. a flexible PET substrate or similar, and shaped during production. The radio chip 135 is typically glued to the substrate, using an electrically conductive glue, or other suitable material or method that allows for maintaining electrical connection while the substrate is bent.

The area between the bottom of the shaped transition 133 and the top layer is filled with an insulating material 122 in order to reduce the effect from ambient temperature, and loss of heat from the measured surface. Such insulating material 122 can be e.g. closed cell polyethylene foam or similar materials. In addition, the reflective layer in the antenna structure 138, can be of e.g. metallized BoPET (Biaxially-oriented polyethylene terephthalate) or similar insulating material in order to reduce the loss of heat from the measured surface. Both insulating techniques in combination with the thermal conductor 114 will help reduce the time for temperature equilibrium for the internal temperature sensor and the sensors 110 or 120. This is achieved as the insulator 122 will reduce the thermal conductivity between the sensor 110 and the ambient conditions, The metal sheet insulator 138 in the antenna 130 will reduce the thermal conductivity for the whole surface area covered by the sensor implementation 100, while the thermal conductor 114 will increase the thermal conductivity to the surface of the medium being measured.

Now referring to FIG. 6. In the heat flux sensor approach, the substrate 180, which can be e.g. a flexible PET substrate, can be assembled as one piece in production, similar to the single sensor approach, but with the external temperature sensor 120 and sound sensor located away from the radio chip 135. An approach for the substrate in the heat flux sensing approach, can be to produce it two times the size of the sensor implementation 100, connect the external sensor 110 using connection wires 182 routed through a cut out or keep out area of the antenna area 139, and with a feature to fold it around a material 122, which serves as the antenna spacer between the metallic reflector 138 and the antenna radiating element 132, and as an insulator reducing heat loss from the surface, features known electromagnetic properties and a known heat transfer coefficient, the material can e.g. be optimized for a more compact antenna design 130, or as a good insulator. Both the thermal conductor 114 and the insulating material 122, both in the single sensing and heat flux sensing approach, will have known thermal properties, and the sensor data from 129, 110 and 120 in combination with the ambient sensor data from the reader 200, an algorithm and signal processing system 370 can estimate the organisms heart sounds, heart rate, oxygen saturation and true core temperature from its surface temperature, applying known compensation techniques from literature, e.g. medical literature for human core temperature estimation. Changes in ambient conditions can be detected by the ambient sensors 270 in the reader 200, before it effect the sensor 110 or 120, and as the effects from ambient to the sensor 110 or 120 in the sensor implementation 100 is known, this effect can be compensated for in the signal processing algorithm system 370.

Figure 9:
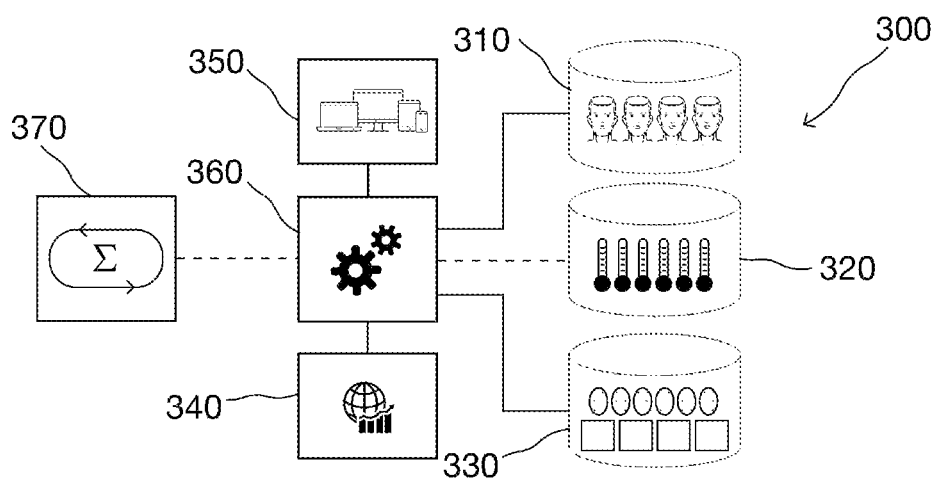
FIG. 9 show essential parts of the ecosystem with interfaces, signal processing algorithms, processing and the different storage systems.

The heart sound and heart rate signal processing system 370, shown in FIG. 9, measures the heart rate, and analyses frequency content and anomalies in the heart sounds looking for known deviating frequency content like e.g. murmur, rumble, clicks and snaps as indicators for illness. Several signal processing techniques are applied to analyse the sound, like e.g. Fast Fourier Transforms FFT, phase detections and wavelet correlations. The oxygen saturation signal processing system 370, shown in FIG. 9, measures the amount and frequency content of reflected light, and calculates the content of oxygen in the blood stream. Several signal processing techniques are applied, like FFT, Weighted Moving Average WMA, and others.

The single temperature sensor signal processing algorithm system 370, shown in FIG. 9, measures the surface temperature of the organism, e.g. the skin temperature of a human, and uses known compensation techniques like wet/dry bulb compensation techniques for moisture e.g. a constantly defined difference between surface and core temperature, combined a temperature leakage compensation to ambient conditions using sensor information from the sensor 270 in the reader 200. The heat flux sensing approach utilizes two sensors 110 and 120 and calculates the core temperature 520 by calculating the heat flux from the core through the tissue and skin 515, using the difference between the two sensors readings and the known heat transfer coefficient 124 of the material 122 in between to calculate the heat flux through the material 122. The following equation can be a central part of such calculation when used to e.g. calculate the core temperature of humans, shown in FIG. 17:

$$T_C = T_A + \frac{h_A}{h_B} * (T_A - T_B)$$ Equation 1

Where:
Tc: The core temperature
TA: The temperature of sensor A 106
TB: The temperature of sensor B 114
$\square_{qCA}$ Heat flux between core and skin 515
: Heat flux between sensor A 106 and sensor B 114
$\square_{qAB}$ Heat transfer coefficient 510 of the tissue/skin
: Heat transfer coefficient 123 of the insulating material 122
$h_A$:
$h_B$:

The reason for the sensor implementation 100 structure: Utilizing known data on heat transfer coefficient of the organism e.g. human body's skin/tissue, an optimized and known thermal conductivity between the skin and the sensor 110 and 120 and 110 in single sensor mode, a known heat transfer coefficient 124 of the insulating material 122 and a known thermal conductivity to the ambient conditions in the sensing environment, an algorithm can be applied to predict the organisms core temperature with high accuracy. The combination of antenna design, shapes to connect the radio chip in the single sensor approach, and folding in the heat flux approach, thermal connection to the sensor, and insulation to the ambient conditions maintains an optimal combination of antenna and sensor performance for long range continuous and passive RFID sensor applications of surface temperature and core temperature estimation in organisms.

The lower layer: The bottom layer located on the same layer as the thermal connection to the measured medium (e.g. skin), will be an adhesive layer 152 with e.g. hypoallergenic properties that does not cause any harm to the organism it is applied on.

The top layer: The top layer will be a printable layer for artwork. This layer will be a thin layer of a material causing no effect to the antenna performance, like thin paper.

Figure 8:
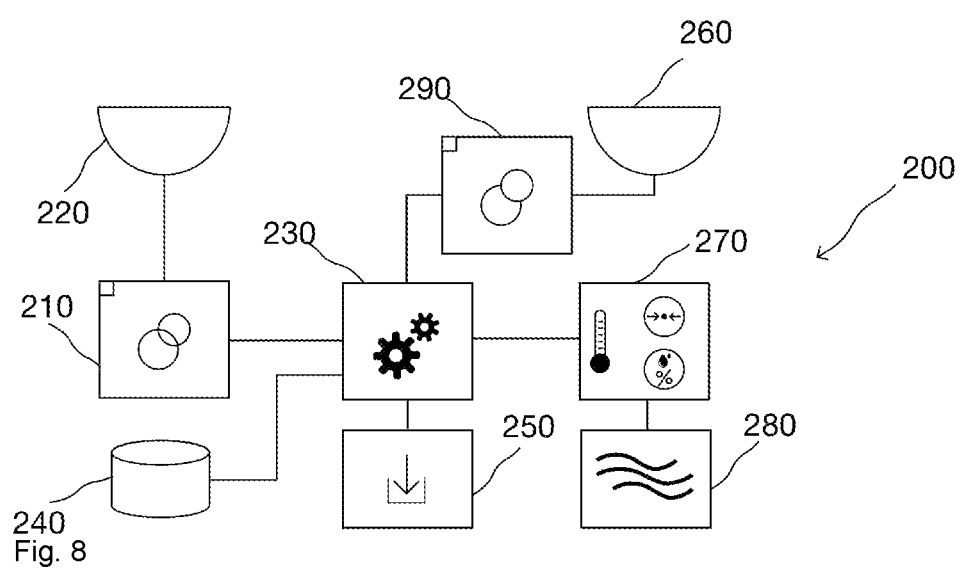
FIG. 8 shows the reader and its antennas, radio chip, processing chip, sensors, interfaces, storage and airflow design.

The Reader 200 (shown in FIG. 8) is designed as a portal to the ecosystem for the radio sensor implementation 100. The design can comprise a radio reader chip 210, a processing unit 230, internal storage 240, internal sensors 270, wired interfaces 250, radio for wireless network interfaces 290, antenna for wireless network interfaces 260, and radio antenna 220 and if the sensor 270 is an air quality and/or temperature sensor, an air flow design for the sensor 280. The reader 200 reads the sensor implementation through a custom read plan, where e.g. radio chips 135 in sensor implementations require, a certain amount of induced energy, which can be ms to accumulate enough power to perform sensing using the internal sensor 110 and/or external sensors 120 and/or others and communicate e.g. the appropriate sensor information, calibration data, ID and other information to the reader 200. Further the reader 200 and read plan is customized in such a way that it is optimized for low power consumption, duty cycling communication to the sensor implementation 100 and hence its measurement frequency, and the communication interval to the ecosystem 300, allowing the reader system to sleep cyclically. Through this implementation a sensor can be read several times sequentially, and oversampling can be applied to increase resolution and reduce noise in measurements, where e.g. temperature change slowly compared to the applied read rate, hence increasing temperature measurement accuracy of the sensors, which following can increase the accuracy of the core temperature calculation. The standard wireless and wired network communication protocols and methods implemented in the reader 200 can work as a single main channel for communication to the ecosystem 300, and e.g. comprise backup systems in case the main communication fails. Further the reader 200 can comprise backup storage to use in case main communication channel fails temporarily, and/or the backup communication channel fails temporarily. The reader 200 may also comprise methods in e.g. hardware or software for encryption of data being communicated to the ecosystem. Through the network connections to the reader 200 e.g. through IP addresses, it can record the current geolocation to the ecosystem for purposes which can be e.g. setting the mode of operation due to regulatory requirements, location and tracking epidemic and non-epidemic illnesses in the society, looking up local environment conditions which can be temperature, humidity and barometric pressure. Further the reader design comprises an air flow design 280, separating the ambient sensors 270 from effects caused by e.g. heating of air inside of reader 200 or dry air inside of reader 200, ensuring a more correct sensing of ambient conditions.

The ecosystem 300 (as shown in FIG. 9) can be designed to e.g. store data on products 330, sensor readings 320 and users 310, as well as comprise signal processing algorithm methods 370, with an implemented algorithm e.g. as described in Equation 1 and a processing unit 360, running the signal processing algorithm methods 370, on the sensor data, using the e.g. equation 1 to calculate the core temperature of the e.g. human being, and other equations to detect heart anomalies, calculate oxygen saturation and heart rate. Further the ecosystem 300 can comprise different interfaces for the user side 350 and big data side 340. Such ecosystem 300 can be implemented as e.g. a network cloud solution or on any other device or unit. The ecosystem 300 can be designed to store the unique ID of all products designed and produced to be a part of the ecosystem 300, which can be e.g. sensor implementations, readers and other devices, limiting counterfeit products to compromise the e.g. user experience and/or quality and usability of the sensor data. In such ecosystem 300 the interface for users 350 could easily limit individual users' access to data, to be the data generated by the user's products only. And the interface for big data could easily limit the data not to comprise user identifiable data, which can be e.g. e-mail addresses, names, notes, images and similar. Further the ecosystem could by storing all unique product IDs in a database, limit operation time of products, to ensure the quality of readings is not compromised by e.g. sensors being used over a long period and e.g. causing faulty data due to reduced audio, electrical and thermal connection with the surface of the organism.

The thermoregulation in an organism is part of a homeostatic mechanism that strives to maintain optimal operating temperature. The temperature is not a constant as it varies during the day, over days and over populations of individuals. In humans the average of such temperature is 37.0° C., however due to the normal rhythms in temperature, the normal temperature is defined as a range: 37.0±0.5° C. A rise in normal temperature can be caused by sever factors, and are divided into two main definitions, fever and hyperthermia. Fever is a condition where the organism's temperature is raised above the normal range, this is known as febrile response or pyrexia. Fever caused by a raised setpoint in the thermoregulation, which mostly happen due to both infectious and non-infectious medical conditions. Hyperthermia on the other hand is caused by a situation where the organism is producing more heat than it can dispose of, which can be caused by ambient conditions with high temperatures (heat stroke), or adverse reactions to drug use. In this situation the setpoint is not raised. Temperatures higher than 37.2° C. in the morning or higher than 37.7° C. in the afternoon are normally considered as fever. The ranges of fever temperatures are classified as: fever >37.5° C., Hyperthermia >37.5° C., and Hyperpyrexia >40.0° C. Hyperpyrexia can be life-threatening and is considered a medical emergency. Fever (or temperature) development over time reveals a certain pattern of fever (fever pattern). These patterns have been known and used to aid diagnosing illness since the antiquity, and are usually classified as: Continuous fever, intermittent fever, Remittent fever, Pel-Ebstein fever, Undulant fever and Relapsing fever.

Figure 10:
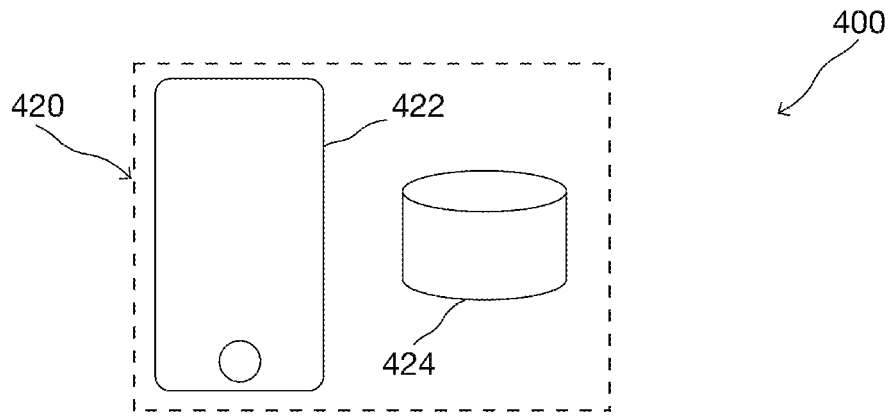
FIG. 10 shows the user device in the system, and the storage unit of such device.
Figure 11:
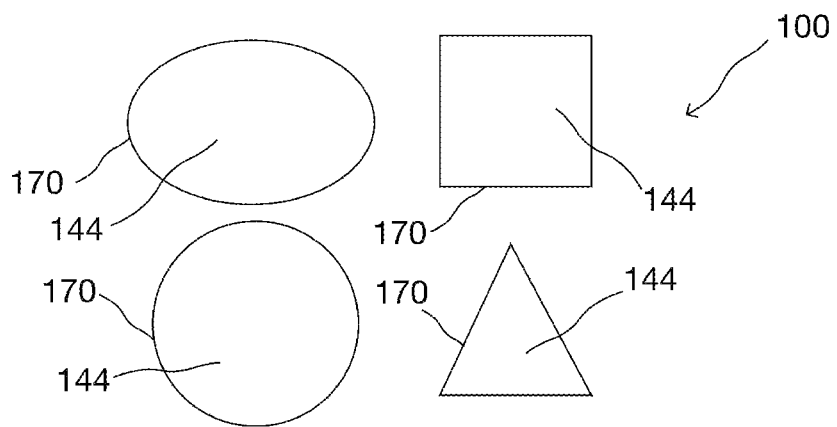
FIG. 11 shows the sensor implementation and examples of shapes.

The end user device 400 (as shown in FIG. 10) comprises an interface designed as an e.g. web interface, application on a smart device or other. This interface 422 can e.g. present real time data from an ongoing measurement, and set and adjust notifications based on the change of this data over time. Such notifications can be e.g. detection of certain heart sounds like murmur, rumble, clicks and snaps, low oxygen saturation alert, high fever alerts, or a given level of fever and elevated heart rate over a long period for humans with a condition causing a febrile reaction. Alerts based on other sensors, like an accelerometer, where a fever seizure alarm can be triggered by the body movements during seizure. History of data e.g. short term or long term and former individual measurements could be accessed through the interface 422. The end user device 420 could comprise a storage unit 424, which could be used to e.g. temporarily store data in case a back up communication solution to the reader is active, and/or there is no connection to the ecosystem 300 or data history or external storage. Further the user interface 422 could comprise a fever reducing drug administration as well as general state of health registration feature, which could comprise a timestamp and which could be a simple graphical button in a graphical user interface, and which could support registration of the actual drug including amount and brand, which could be implemented as a software correlating camera input from e.g. a smart device used to scan a optically readable product code on such drug packaging and correlate such information to public drug databases. Such information on drug administration could then be used in e.g. correlation with the sensor data to explain e.g. unexpected changes over time and the amount of drug administration in addition to the general state of health to a e.g. a medical doctor when analyzing human illness data provided by the system. Further the end user device 400 could comprise a radio reader chip to induce power to and read data from the sensor implementation 100 directly. This could be performed using e.g. NFC, RFID etc.

Figure 12:
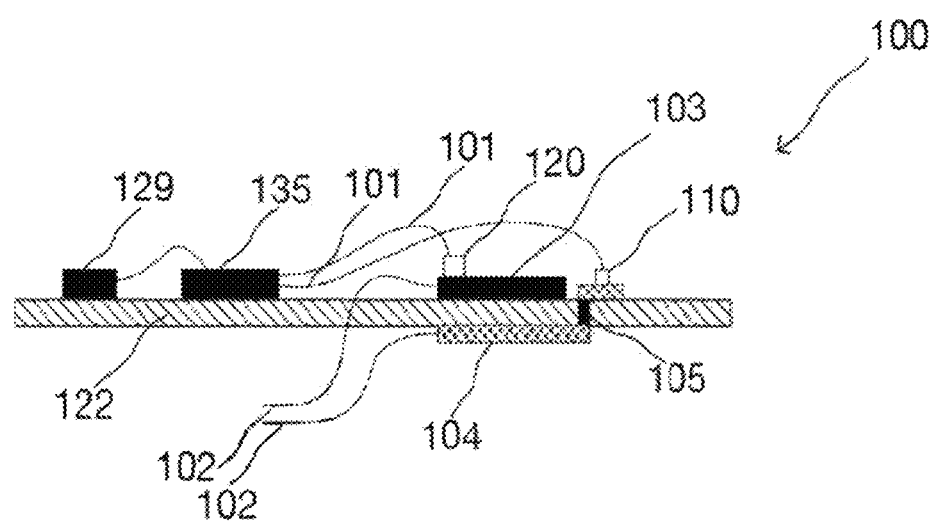
FIG. 12 shows the sensor implementation with radio chip, sound sensor, and a heat flux sensor build using two thermistors, thermally conductive and thermally insulating materials.
Figure 13:
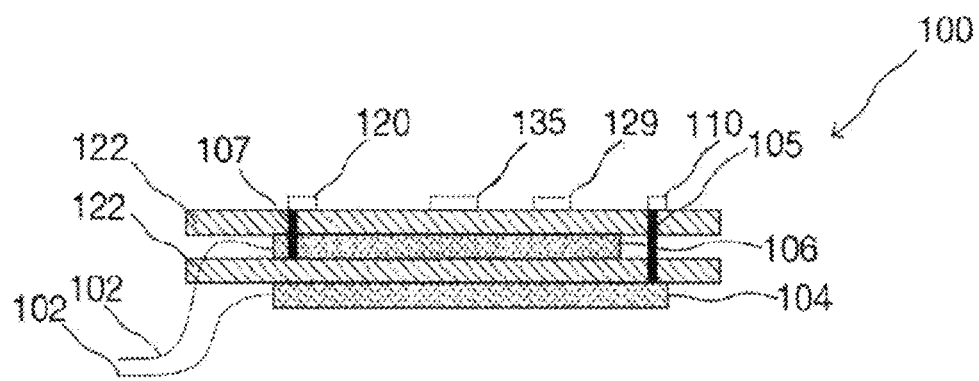
FIG. 13 shows the sensor implementation with radio chip, sound sensor, and a heat flux sensor build using a multi layer structured material, like standard PCB providing the thermally conductive and thermally insulating materials.
Figure 14:
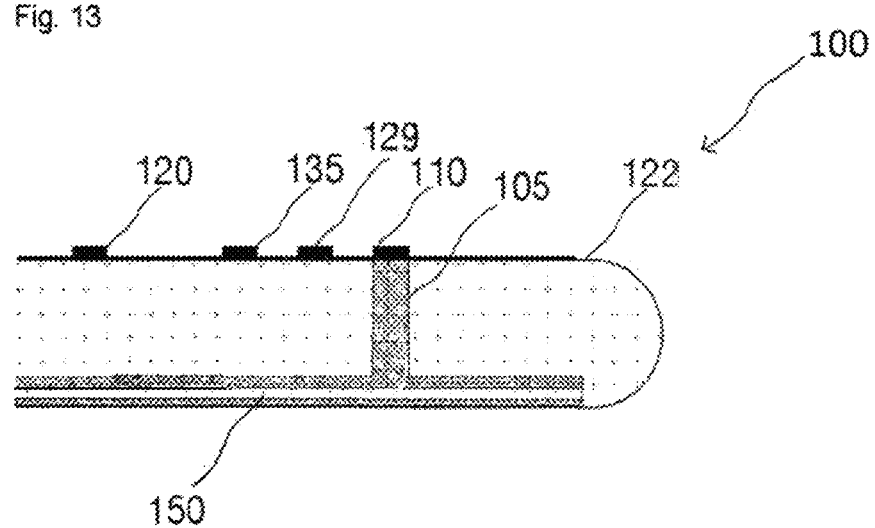
FIG. 14 shows the sensor implementation with radio chip, sound sensor, and a heat flux sensor build using two thermistors, where the components are assembled on a flexible substrate which is folded around a thermally insulating material with an additional functionality as an energy storage device.
Figure 15:
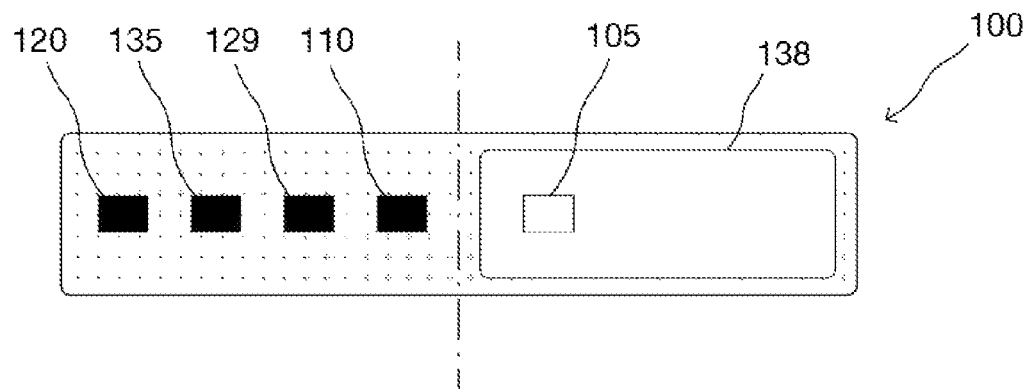
FIG. 15 shows the sensor implementation with radio chip, sound sensor, and heat flux sensor build using two thermistors, where the components are assembled on a flexible substrate, showing the heat pipe connecting the contact surface to one of the thermistors.

In FIG. 13 a second embodiment of a sensor implementation is shown. The sensor implementation 100 is built as a multi-layer structure to combine properties of long range backscatter communication and optimized sensing conditions, incorporating energy storage in the multi layer structure and energy harvesting from the environment. The sensor implementation 100 comprises an antenna 130, a radio chip 135 which could comprise both an integrated power harvesting unit 140, and temperature sensing functionality using two thermistors 110 and 120, a sound sensor 129 and a instrumental amplifier for e.g. ECG, light emitter 119 and light sensor 118 and a radio and protocol part, including a possible interface to e.g. power and communication with external sensors, which can be temperature sensors. A Thermal conductive layer 104, a thermally insulating layer 122, and a print layer 144. The sensor implementation may also comprise an external energy harvesting unit 140, comprising one or more means for harvesting energy from its surroundings. An area on the antenna layer 142 (see FIG. 16) can be dedicated to energy harvesting, allowing implementation of e.g. energy harvesting antenna structures and solar panels, harvesting electromagnetic and light energy. In FIG. 12, 13, 14 various embodiments of the sensor build up is shown. The sensor build for heat flux sensing is built with a thermally conductive layer 104, in contact with the contact surface, and with a temperature sensor 110, connected thermally with a piece of good thermal conductor 105, like metal, going through the thermal insulator 122. The piece of thermal conductor 105 and on the top of the insulator material, hence they are located on the same layer, enabling the second temperature sensor 120 to be located on top of the insulator 122, thus temperature sensor 110 and 122 represent a heat flux measurement while being located on the same layer, on the same layer a sound sensor 129 is also located, allowing less complex and lower cost production. Further the thermally conductive layer 104 double up as a part of the antenna, serving as a reflector, reducing energy absorption from the human skin. Said layer can be implemented as a multi layer metal structure, where the metal layers are implemented as thin sheets, separated by thin sheets of an isolator material with good thermally conducting properties. Said multi layer structure 104, 106 hence also serves as a energy storage device and are connected to the energy harvesting engine 140.

FIG. 12 shows the thermally conductive layer 104 in the sensor implementation 100 enables direct and good thermal contact with the surface, e.g. human skin the sensor implementation 100 is placed on. The thermally conductive layer 104 will be in direct contact with the measured medium, and the sensor 110 through a heat pipe 105 implementation, while sensor 120 is located on top of the thermal insulator 122 forming a heat flux sensor.

Figure 16:
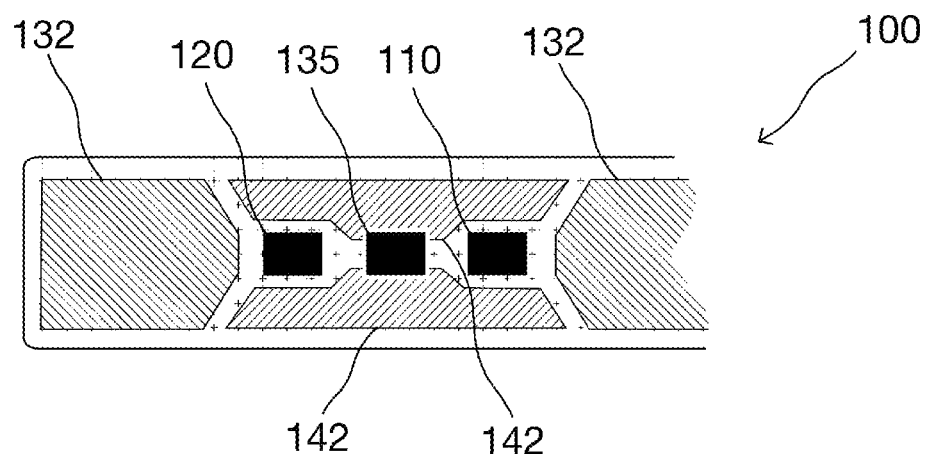
FIG. 16 shows the radio chip and the two thermistors on the layer together with the areas dedicated for communication antennas and energy harvesting.
Figure 17:
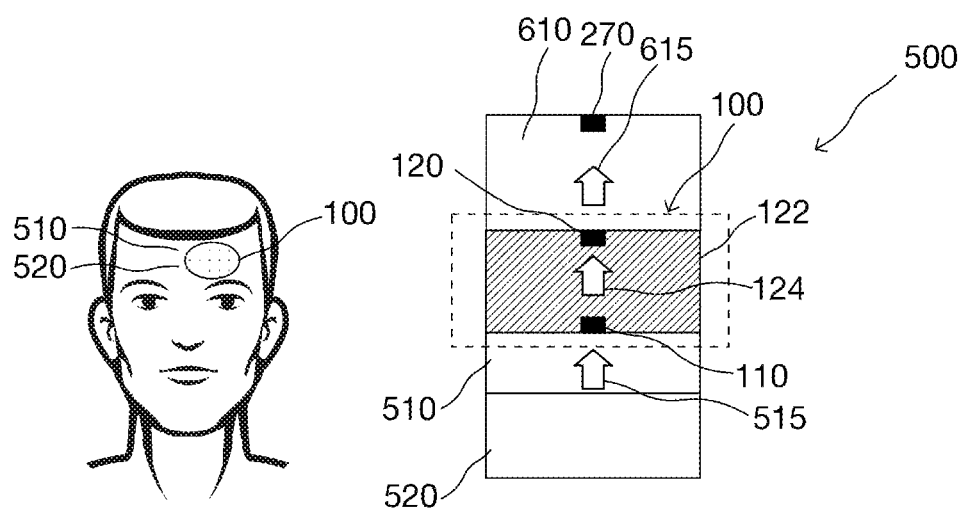
FIG. 17 shows concepts and parts for heat flux mode temperature measurement and reference to core temperature. Including the heat flux channel to ambient.

In FIG. 16 the substrate comprising the antenna radiating element 130, power harvesting element 142, temperature sensors 110 and 120 and radio chip 135 can be designed as one piece, assembled on e.g. a flexible PET substrate or similar, and shaped during production. Enabling low cost roll to roll production. The components are typically glued to the substrate, using an electrically conductive glue, wire-bonding or other suitable material or method that allows for maintaining electrical connection while the substrate is bent.

Insulating material used in contraction with said flexible substrate can be e.g. closed cell polyethylene foam or similar materials.

In FIG. 7 a second heat flux sensor approach is shown, the substrate 122, which can be e.g. a flexible PET substrate, can be assembled as one piece in production. Both the thermal conductor 104 and the insulating material 122 in heat flux sensing will have known and constant thermal properties, and the sensor data from 110 and 120 in combination with the ambient sensor data from the reader 200, an algorithm and signal processing system 370 can estimate the organisms true core temperature from the heat flux sensor data. Changes in ambient conditions like e.g. temperature, humidity and barometric pressure can be detected by the ambient sensors 270 in the reader 200, before it affect the heat flux sensor, and as the effects from ambient to the heat flux sensor in the sensor implementation 100 is known, this effect can be compensated for in the signal processing algorithm system 370.

The heat flux sensing approach utilizes two sensors 110 and 120 and calculates the core temperature 520 by calculating the heat flux from the core through the tissue and skin 510, using the difference between the two sensors readings and the known heat transfer coefficient of the material 122 in between to calculate the heat flux through the material 122. The following equation can be a central part of such calculation when used to e.g. calculate the core temperature of humans, shown in FIG. 17. The calculations are using the equation 1 mentioned earlier.

The reason for the sensor implementation 100 structure: Utilizing known data on heat transfer coefficient of the organism e.g. human body's skin/tissue, an optimized and known thermal conductivity between the skin and the sensor 110 and 120, a known heat transfer coefficient of the insulating material 122 and a known thermal conductivity to the ambient conditions in the sensing environment, an algorithm can be applied to predict the organisms core temperature with high accuracy. The combination of sensor implementation in a compact multilayer structure, utilizing antenna reflector and antenna radiating structure as energy storage devices, and utilizing the antenna reflector as a heat transfer design, allow the Heat flux approach to be implemented in a compact low cost form factor. Combining the antenna design for backscatter radio with energy harvesting, energy storage features and the sensor build maintains an optimal combination of antenna and sensor performance for long range continuous and passive backscatter radio sensor applications of core temperature estimation in organisms.

The lower layer: The bottom layer located on the same layer as the thermal connection to the measured medium, will be an adhesive layer 152, e.g. a Silicone Gel Adhesive with hypoallergenic properties that does not cause any harm to the organism it is applied on, as well as being waterproof and resistant to bacteria. The adhesive is preferably thin and thermally conducting with known thermal conductive properties.

The top layer of the sensor implementation: The top layer will be a printable layer for artwork. This layer will be a thin layer of a material causing no effect to the antenna performance, like thin paper.

Figure 18:
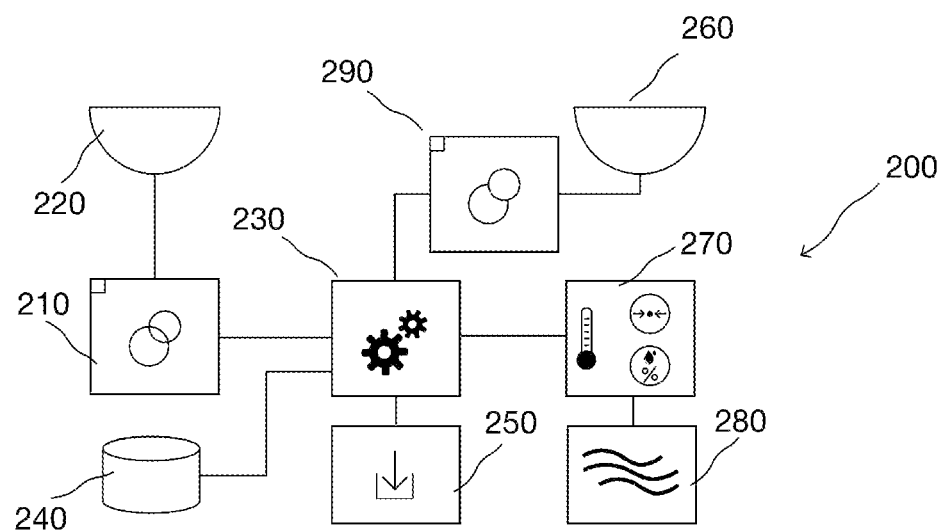
FIG. 18 shows the reader and its antennas, radio chip, processing chip, sensors, interfaces, storage and airflow design.

FIG. 18 shows a second embodiment of The Reader 200 is designed as a portal to the ecosystem for the radio sensor implementation 100. The design can comprise a radio reader chip 210, a processing unit 230, internal storage 240, internal sensors 270, wired interfaces 250, radio for wireless network interfaces 290, antenna for wireless network interfaces 260, and radio reader antenna 220 and if the sensor 270 is an air quality and/or temperature sensor, an air flow design for the sensor 280. The reader 200 reads the sensor implementation through a custom read plan, where e.g. radio chips 135 in sensor implementations require several time units of induced signals which can be ms to accumulate enough power to perform sensing using the sensors 110 and 120 and communicate e.g. the appropriate sensor information, calibration data, ID and other information to the reader 200. Further the reader 200 and read plan is customized in such a way that it is optimized for low power consumption, duty cycling communication to the sensor implementation 100 and hence its measurement frequency, and the communication interval to the ecosystem 300, allowing the reader system to sleep cyclically. Through this implementation a sensor can be read several times sequentially, and oversampling can be applied to increase resolution and reduce noise in measurements, like temperature, which change slowly compared to the applied read rate, hence increasing temperature measurement accuracy of the sensors, which following can increase the accuracy of the core temperature calculation. The standard wireless and wired network communication protocols and methods implemented in the reader 200 can work as a single main channel for communication to the ecosystem 300, and e.g. comprise backup systems in case the main communication fails. Further the reader 200 can comprise backup storage to use in case main communication channel fails temporarily, and/or the backup communication channel fails temporarily. The reader 200 may also comprise methods in e.g. hardware or software for encryption of data being communicated to the ecosystem. Through the network connections to the reader 200 e.g. through IP addresses, it can record the current geolocation to the ecosystem for purposes which can be e.g. setting the mode of operation due to regulatory requirements, location and tracking epidemic and non-epidemic illnesses in the society, looking up local environment conditions which can be temperature, humidity and barometric pressure. Further the reader design comprises an air flow design 280, separating the ambient sensors 270 from effects caused by e.g. heating of air or dry air inside of reader 200, ensuring a more correct sensing of ambient conditions.

Figure 19:
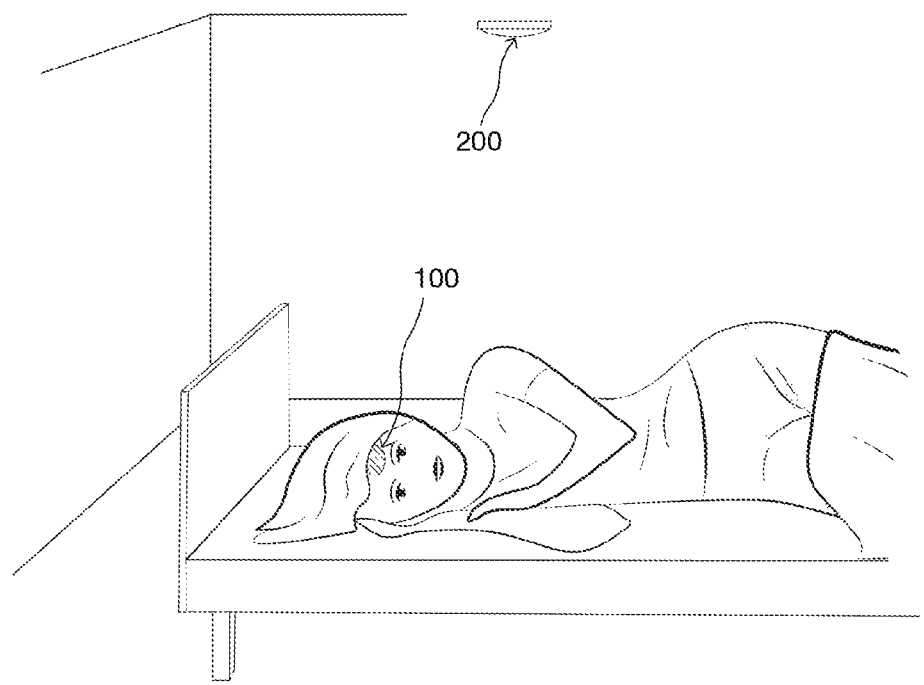
FIG. 19 shows a typical user scenario with a reader in ceiling and sensor on user forehead.

FIG. 19 shows a typical scenario where a reader 200 is located in the ceiling and a sensor 100 is attached to the forehead of a patient.

Figure 20:
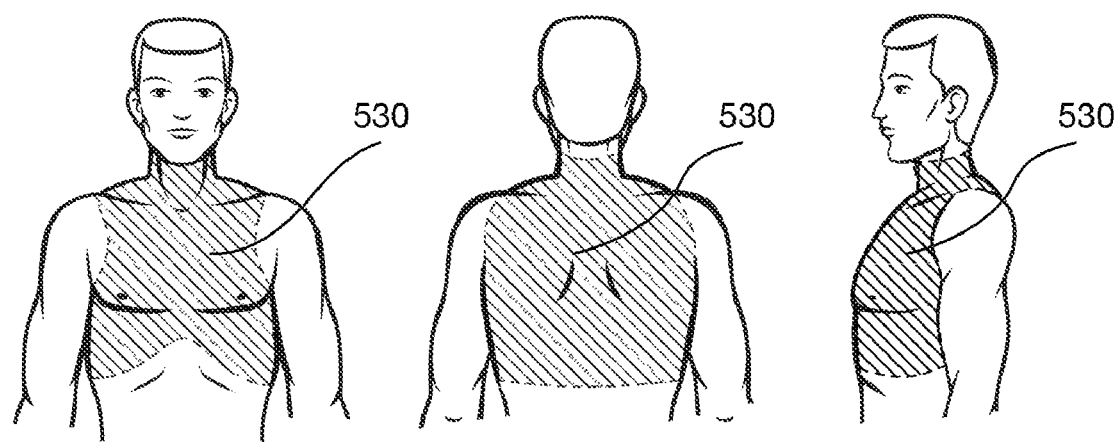
FIG. 20 shows the upper human body and the indication of the thorax.

FIG. 20 shows the human upper body and indicates the Thorax, which is the typical area where heart sounds and heart rate are predominant. this indicates the optimal area to place the sensor 100.

Figure 21:
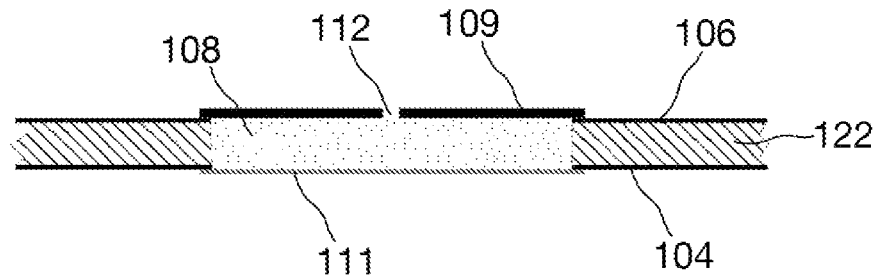
FIG. 21 shows the sound sensor implementation as a capacitor in a standard substrate stack-up.

FIG. 21 shows a sound sensor implementation in a substrate like e.g. standard PCB, where the first layer 104 and third layer 106 represent top layers on each side of a 2 layer PCB stackup. The substrate 122, represent the core in the PCB. 108 is a hole machined out in the PCB, forming a air cavity in between the diaphragm 111 and metal back plate 109. The conductive diaphragm 111 and the metal back plate with the cavity in between, will work as an capacitor. This capacitor is designed to be greatly affected by the movement of the diaphragm 111 due to sound waves picked up by the diaphragm 111. As the diaphragm 111 moves, air is let in and out of the cavity through the perforation 112. The change in capacitance between 109 and 111 caused by sound waves can thus be detected.

Figure 22:
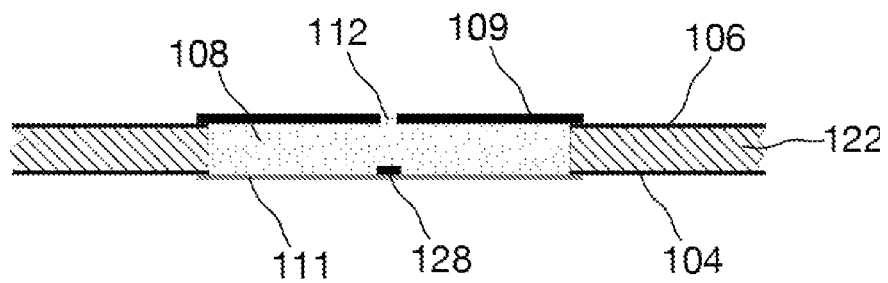
FIG. 22 shows the sound sensor implementation as a capacitor in a standard substrate stack-up incorporating an accelerometer.

FIG. 22 shows the same implementation as in FIG. 21, only with a addition of a accelerometer 128 placed in the center of the diaphragm 111. This way the sound waves picked up by the diaphragm 111 can be read by the change in capacitance and the accelerometer 129 data.

Figure 23:
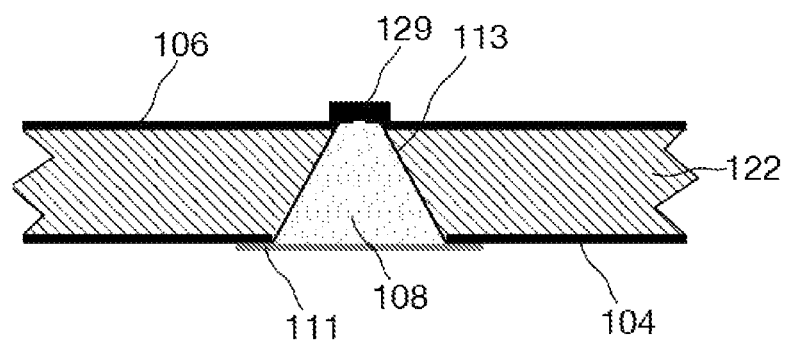
FIG. 23 shows the sound sensor implementation with a conical shaped air cavity, a diaphragm, and a sound sensor in a multi-layered structure.

FIG. 23 shows a sound sensor implementation in a multi layered structure like e.g. standard PCB, where the first layer 104 is in contact with e.g. the skin. Starting from the first layer 104, and all the way through the substrate 122, a cone shaped air cavity 113 is machined out. The tip of this cone punctures the third layer 106, leaving a small hole. A diaphragm 111 is mounted covering the wide end of the air cavity 113, on the first layer 104 side of the structure. On the third layer 106 of the structure, a sound sensor 129, e.g. a MEMS microphone is placed directly on top of the small hole in the third layer 106. The resulting effect is that sound waves that makes the diaphragm 111 move cause these sound waves to travel through the cavity 113, which are picked up by the sound sensor 129.

Figure 24:
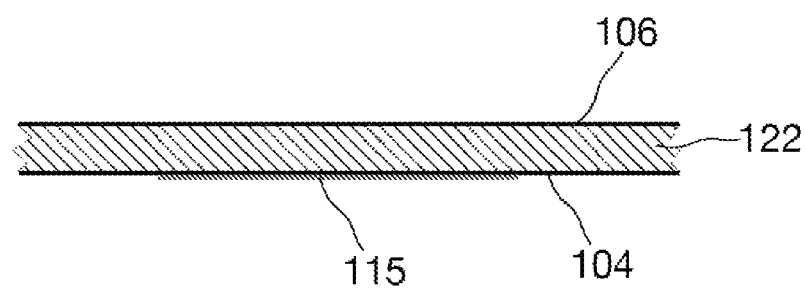
FIG. 24 shows the sound sensor implementation as a force sensor on the first layer of a multi-layered structure

FIG. 24 shows a sound sensor implementation as a force sensor 115 on the first layer 104 of a multi layered structure like e.g. standard PCB. Such force sensor 115 can be a e.g. capacitor designed to be sensitive to force, or e.g. a thin piezoelectric element.

Figure 25:
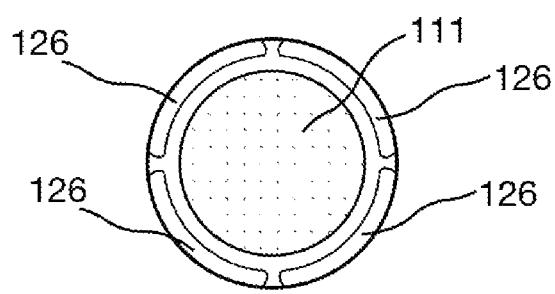
FIG. 25 shows the diaphragm surrounded by electrodes on the first layer of a multi-layered structure.

FIG. 25 shows the first layer 104 and the diaphragm 111 surrounded by 4 electrodes 126 which are connected to an operational amplifier picking up voltage fluctuations, the ECG.

Figure 26:
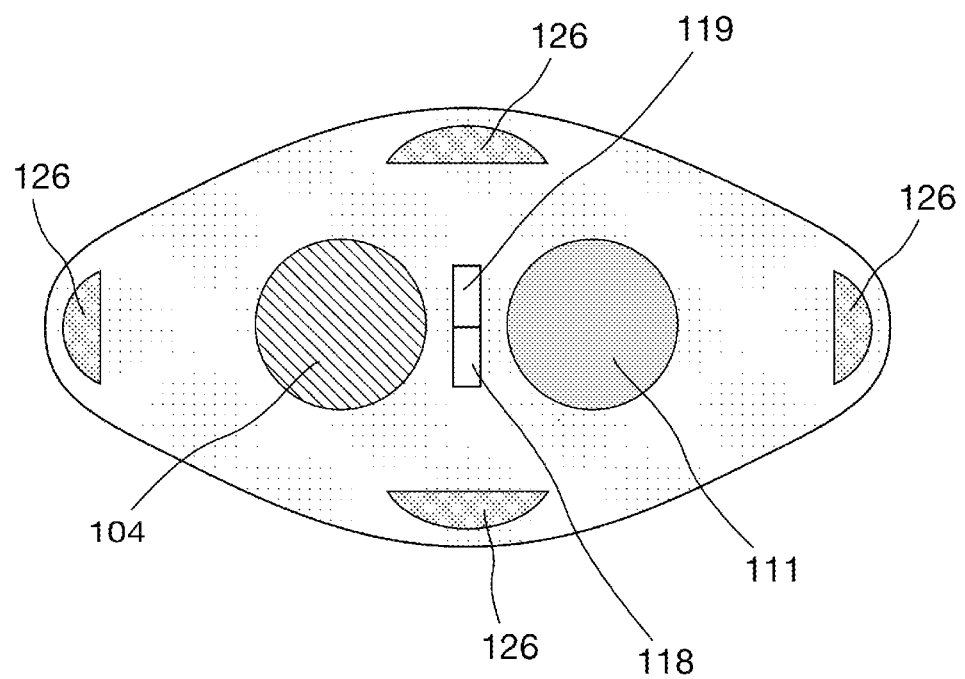
FIG. 26 shows the structural side facing the e.g. skin of a human, and the electrodes, temperature conducting layer, diaphragm, light sensor and light emitter in contact with the e.g. skin.
Figure 27:
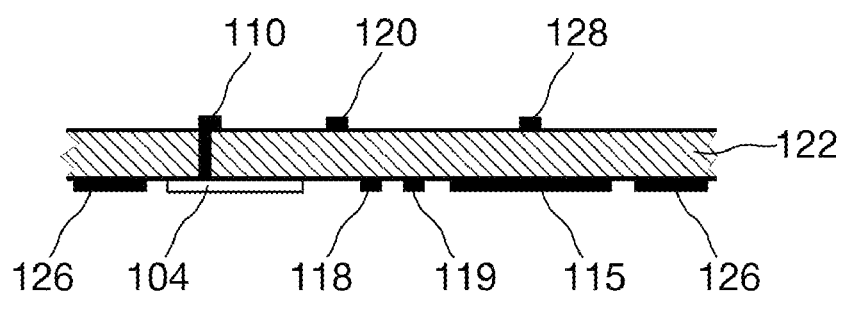
FIG. 27 shows the multilayer structure around the substrate, and the electrodes, temperature conducting area with heat pipe, light emitter and light sensor, force sensor facing the e.g. skin of a human, and the temperature sensors and accelerometer assembled on the structurally opposite side.

FIG. 26 shows the first structural side in contact with the e.g. skin of a human, and the first layer 104, the diaphragm 111, the electrodes for ECG measurements 126, and the light emitter 119 and light sensor 118.

FIG. 126 shows a cross section with the electrodes 126, the first layer 104 in thermal contact with the temperature sensor 110, the light sensor 118 and light emitter 119, the force sensor 115, the substrate 120, the second temperature sensor 120, and the Accelerometer 128.

An algorithm taking into account BT, HR, RR and other sensor function to detect the characteristic changes for particular diet.

Alternative Embodiments

A number of variations on the above can be envisaged. For instance using an antenna 130 in the wireless sensor implementation, where the antenna is designed by those skilled in the art to operate on the surface of the organism e.g. human skin, and not in air.

Another variation is to design the antenna 130 in such a way that it uses the organism or parts of the organism constructively e.g. like the frontal skull bone in a human cranial, to improve antenna performance.

Another variation can be implementing the wireless sensor system in a different substrate material and shape, designed to be used on in different ways on an organism. For a human this can be e.g. a contact lens, shirt or an earplug, earring or other jewelry, or implemented in shoes, clothing fabric, bandages, elastic bands, medical casts or plaster, briefs, diapers, sanitary pads, pantyliners, prosthesis, corsets or other medical and non medical support or aid devices.

Another variation of this could be a wireless sensor implementation using multiple radio protocols and standards, allowing a wider range of use and operating ranges. This can e.g. be multiple radio protocols, a combination between existing and new radio protocols, custom protocols based on the latter, or multiple other radio protocols.

In some embodiments of the sensor in use for elderly patients a combination of a optical sensor, capacitive sensor, moisture and a chemical sensor like a PH sensor, implemented in e.g a brief, would provide means for higher quality of living for the elderly and better quality assurance for routines in a e.g. elderly care home. A sensor combination like this would be able to classify content of the brief in addition to detect early indications on several medical and non medical conditions like; acidosis, dehydration, diarrhea, starvation, kidney failure and urinary tract infection.

In other embodiments a combination of ECG, microphone, temperature, pressure, proximity, orientation, displacement, light, capacitance and acceleration implemented as a sensor system could e.g. detect the use of medical support aids, if located in between the skin and a e.g. corset used post surgery on many back and neck injuries and post correcting surgery from birth defects. This system would then be able to detect amount of use, if used correctly e.g too tight or too loose, patient movement and activity during use, and support aid displacement during use. Giving a medical doctor a data foundation to support and aid further patient advice, treatment and motivation for improved results.

In yet other embodiments a combination of sensors combining temperature, moisture and light, e.g. ultraviolet light, could serve as a sensor system detecting hyperthermia/overheating and overexposure to sunlight for children and elderly. In some embodiments one or more temperature sensors can be combined with a bio impedance sensor, the system can then also detect dehydration.

In yet other embodiments the sensor is combined with one or more sensors from the group comprising temperature sensing, moisture and PH levels in combination with bio impedance could serve as smart bandages for e.g. burns, detecting if the wound needs attention due to; increased surface temperature relative to core and/or fever due to infections, changing PH levels due to certain bacteria infections and increased moisture due to discharge from bacteria growth. Would enable a caretaker to avoid changing bandages when not needed, causing unnecessary need for new infections by breaking the scab seal protecting the development of new skin.

In other embodiments the sensor system can be combined with sensors like audio, noise, sound, and an accelerometer as this would serve as a e.g. snoring and apnea detector, combining audio and vibration to provide low cost tests for the home health care market.

In yet other embodiments a combination of sensors like temperature, accelerometer, displacement and force would e.g. provide means of detecting joint flexibility and use after a e.g. knee meniscus surgery, and even detecting local temperature development caused by infection or inflammation in the knee. Providing the patient and doctor information to improve care and restitution.

In yet other embodiments images is captured of the patient's fever rash, blushing, skin colour. This is used together with temperature patterns and other vital data gathered from the patient to monitor patient. Temporal development of the rash can be used to determine illness together with fever pattern.

The thermally insulating layer 122 can double as an electrically insulating material, as an alternative to a separate thermally insulating layer and an electrically insulating material that can be stacked.

A number of further variations of such system can be envisaged. For instance a system notification algorithm detecting RR, HR and user notifications "Tapping" when eating can be used to detect when a person eating is choking on food, to give an alarm in e.g. and elderly care institution, preventing death by choking.

Another variation can be the effect of athletes and Performance/Rest balance monitoring for optimal effect from training. Such implementation can apply the same sensor data in an algorithm designed to map performance and rest indexes for professional athletes through BT, RR, HR and other sensors. Output from such system can be e.g. individual advice on amount of rest between training sessions.

Another variation can be to monitor the dietary intake of psychiatric and elderly patients to maintain over all stability and good health. Such implementation is the same the initial description, only with an algorithm output simplified to indicate sufficient dietary intake to maintain a healthy life. Changes can be notifications to caretakers and family.

The invention claimed is:

1. Sensor apparatus for measuring heart sounds, circulatory effects and core temperature of an organism, the sensor apparatus comprising:
    a first layer with electrodes configured to be in electrical connection with the organism,
    a second layer comprising a thermally insulating material and placed on top of the first layer,
    a third layer provided on top of the second layer,
    a first temperature sensor in thermal connection with the first layer via a thermal conductor through the second layer,
    a second temperature sensor configured to be thermally insulated from the organism and in thermal connection with the third layer, wherein the first and second temperature sensors are located above the second layer,
    a sensor instrumental amplifier ECG device operatively connected to the electrodes, located on the first layer, wherein the electrodes function as ECG electrodes, and
    a sound sensor located on the third layer at the top of a cut out of the first and second layer, forming a cavity for sound to more optimally travel to the sound sensor.

2. The sensor apparatus according to claim 1, wherein the second temperature sensor is configured to be thermally insulated by the second layer from the organism.

3. The sensor apparatus according to claim 1, wherein the second temperature sensor is configured to be thermally insulated by the second layer from the organism by the second layer and the cut out has a conical shape.

4. The sensor apparatus according to claim 1, further comprising at least one additional sensor measuring additional physical property of the group comprising temperature, pressure, fluid flow, heat flow, level, proximity, displacement, bio impedance, image, light, gas, chemical, acceleration, orientation, humidity, moisture, impedance, capacitance, force, electrical, magnetic, mass, and audio.

5. The sensor apparatus according to claim 1, wherein the third and first layer comprises metallic material.

6. The sensor apparatus according to claim 1, further comprising a diaphragm configured to separate the organism and the Cavity.

7. The sensor apparatus according to claim 6, wherein the diaphragm comprises a material that resonates with body sounds, creating acoustic pressure waves to be picked up by the sound sensor.

8. The sensor apparatus according to claim 1, wherein the sound sensor is an accelerometer.

9. The sensor apparatus according to claim 1, further comprising a LED and a light sensor on the first layer configured to point into the surface of the organism.

10. The sensor apparatus according to claim 1, further comprising a diaphragm configured to be in connection with a surface of the organism.

11. The sensor apparatus according to claim 10, wherein the diaphragm comprises an electrically conducting material, and built as a capacitive sensor in a multilayer structure.

12. The sensor apparatus according to claim 11, wherein the third layer comprises an electrically conducting shape directly above the diaphragm creating a capacitor.

13. The sensor apparatus according to claim 12, wherein at least parts of the second layer between the diaphragm and third layer conducting shape are removed, creating an air filled cavity for the diaphragm to move.

14. The sensor apparatus according to claim 13, wherein the diaphragm is made of a piezoelectric element, or comprise an accelerometer mounted on it.

15. The sensor apparatus according to claim 1, wherein the first layer is thermally connected with the first temperature sensor, and electrodes, a force sensor and a light sensor configured to contact a surface of the organism.

16. The sensor apparatus according to claim 1, further comprising a harvester for harvesting electrical energy and at least one energy storage unit, wherein the harvested energy is stored in the energy storage unit.

17. The sensor apparatus according to claim 16, wherein the energy is harvestable from the surroundings using means from the group comprising photovoltaic, thermoelectric, piezoelectric, electromagnetic, magnetic, electric, oxidation, electrostatic, and bio-energy.

18. The sensor apparatus according to claim 1, further comprising a harvester for harvesting electrical energy and wherein the energy is harvested from a diaphragm sensor comprising a piezoelectric element.

19. The sensor apparatus according to claim 1, further comprising a processor for sampling ECG sensors, the first and second temperature sensor, the sound sensor and a light sensor.

20. The sensor apparatus according to claim 1, further comprising an energy storage unit of a type from the group comprising capacitive storage formed of at least two metallic layers and at least one insulating layer of the sensor, a battery, and a fuel cell.

21. The sensor apparatus according to claim 1, wherein the sensor apparatus further comprises a radiating element wherein the first layer is a reflector for the radiating element, and wherein an insulating material creates a distance between the radiating element and the reflector.

22. The sensor apparatus according to claim 21, wherein the radiating element, the insulating material, and the reflector form an energy storage unit for storing harvested energy.

23. The sensor apparatus according to claim 21, wherein the reflector comprises part of a capacitive storage device for storing harvested energy from a harvester.

24. The sensor apparatus according to claim 21, wherein the radiating element functions as a receiving element for energy harvesting.

25. The sensor apparatus according to claim 1, further comprising a processor operatively coupled to at least one selected from the group comprising an energy harvester, energy storage unit, and capacitive storage device for powering the processor to sample data from at least one sensor and the processor is coupled to a radiating element for transmission of at least one sampled sensor data.

26. The sensor apparatus according to claim 25, further comprising an indicator coupled to the processor.

27. The sensor apparatus according to claim 1, further comprising a notification device for notifications and alarms.

28. The sensor apparatus according to claim 27, wherein the notification device for notifications and alarms is at least one from the group comprising button and sound sensor.

29. The sensor apparatus according to claim 27, wherein the notifications and alarms are used to timestamp data of an event.

30. The sensor apparatus according to claim 27, wherein the notification and alarm are used to call for assistance.

31. Sensor apparatus for measuring heart sounds, circulatory effects and core temperature of an organism, the sensor apparatus comprising:
 a first layer with electrodes configured to be in electrical connection with the organism,
 a second layer comprising a thermally insulating material and placed on top of the first layer,
 a third layer provided on top of the second layer,
 a first temperature sensor in thermal connection with the first layer via a thermal conductor through the second layer,
 a second temperature sensor configured to be thermally insulated from the organism and in thermal connection with the third layer, wherein the first and second temperature sensors are located above the second layer,
 a sensor instrumental amplifier ECG device operatively connected to the electrodes, located on the first layer, wherein the electrodes function as ECG electrodes,
 a sound sensor located on the third layer at the top of a cut out of the first and second layer, forming a cavity for sound to more optimally travel to the sound sensor, wherein the first layer is configured to be in electrical contact with the organism, and wherein the sensor is an Electrocardiograph (ECG), and
 wherein the ECG sensor has two or more electrodes separated in the first layer and configured to be in contact with the organism.

* * * * *